(12) United States Patent
Elhag et al.

(10) Patent No.: US 7,648,463 B1
(45) Date of Patent: Jan. 19, 2010

(54) MONITORING DEVICE, METHOD AND SYSTEM

(75) Inventors: Sammy I Elhag, San Diego, CA (US);
Nikolai Rulkov, San Diego, CA (US);
Mark Hunt, San Diego, CA (US);
Donald Brady, Las Vegas, NV (US);
Steve Lui, San Diego, CA (US)

(73) Assignee: Impact Sports Technologies, Inc., Las Vegas, NV (US)

( * ) Notice: Subject to any disclaimer, the term of this patent is extended or adjusted under 35 U.S.C. 154(b) by 356 days.

(21) Appl. No.: 11/566,228

(22) Filed: Dec. 3, 2006

Related U.S. Application Data

(63) Continuation-in-part of application No. 11/304,121, filed on Dec. 15, 2005.

(60) Provisional application No. 60/834,643, filed on Aug. 1, 2006, provisional application No. 60/840,826, filed on Aug. 29, 2006.

(51) Int. Cl.
*A61B 5/02* (2006.01)

(52) U.S. Cl. ............... 600/504; 600/500; 600/502; 600/503; 482/8; 351/41

(58) Field of Classification Search .......... 600/500–504
See application file for complete search history.

(56) References Cited

U.S. PATENT DOCUMENTS

| | | | |
|---|---|---|---|
| 4,380,240 A | 4/1983 | Jobsis et al. | |
| 4,788,983 A | 12/1988 | Brink et al. | |
| 4,800,495 A | 1/1989 | Smith | |
| 4,807,630 A | 2/1989 | Malinouskas | |
| 4,825,879 A | 5/1989 | Tan et al. | |
| 5,213,099 A | 5/1993 | Tripp, Jr. | |
| 5,431,170 A | 7/1995 | Mathews | |
| 5,735,800 A | 4/1998 | Yasukawa et al. | |
| 5,877,446 A | 3/1999 | Monahan et al. | |
| 5,925,841 A | 7/1999 | Rossum | |
| 5,928,342 A | 7/1999 | Rossum et al. | |
| 6,018,673 A | 1/2000 | Chin et al. | |
| 6,425,018 B1 | 7/2002 | Kaganas et al. | |
| 6,431,705 B1 * | 8/2002 | Linden | 351/158 |
| 6,470,199 B1 | 10/2002 | Kopotic et al. | |
| 6,556,852 B1 | 4/2003 | Schulze et al. | |
| 6,599,251 B2 | 7/2003 | Chen et al. | |
| 6,605,038 B1 | 8/2003 | Teller et al. | |
| 6,616,613 B1 | 9/2003 | Goodman | |
| 6,678,543 B2 | 1/2004 | Diab et al. | |
| 6,681,454 B2 | 1/2004 | Modgil et al. | |
| 6,720,734 B2 | 4/2004 | Norris | |
| 6,799,226 B1 | 9/2004 | Robbin et al. | |
| 6,808,473 B2 | 10/2004 | Hisano et al. | |

(Continued)

*Primary Examiner*—Robert L Nasser
*Assistant Examiner*—Michael D'Angelo
(74) *Attorney, Agent, or Firm*—Clause Eight IPS; Michael Catania

(57) ABSTRACT

A monitoring device (20) and method (200) for monitoring the health of a user is disclosed herein. The monitoring device (20) preferably includes eyewear (25) with an optical sensor (30), a digital storage and processing device (35) with a display member (40) and a control component (43), and a connection cable (45). The monitoring device (20) preferably displays the following information about the user: pulse rate; calories expended by the user of a pre-set time period; target zones of activity; time; and distance traveled.

7 Claims, 19 Drawing Sheets

U.S. PATENT DOCUMENTS

| | | |
|---|---|---|
| 6,813,511 B2 | 11/2004 | Diab et al. |
| 6,853,955 B1 | 2/2005 | Burrell et al. |
| 7,179,228 B2 | 2/2007 | Banet |
| 7,187,960 B2 * | 3/2007 | Abreu ..................... 600/310 |
| 7,255,437 B2 * | 8/2007 | Howell et al. ............. 351/158 |
| 7,376,238 B1 * | 5/2008 | Rivas et al. ............... 381/381 |
| 2002/0109600 A1 | 8/2002 | Mault et al. |
| 2005/0094496 A1 * | 5/2005 | Ozawa ...................... 368/184 |
| 2005/0113705 A1 * | 5/2005 | Fischell et al. ............ 600/515 |
| 2006/0084851 A1 * | 4/2006 | Lee et al. .................. 600/301 |
| 2007/0244398 A1 * | 10/2007 | Lo et al. ................... 600/500 |

* cited by examiner

MONITORING DEVICE, METHOD AND SYSTEM

CROSS REFERENCES TO RELATED APPLICATION

The present application is a continuation-in-part application of U.S. patent application Ser. No. 11/304,121, filed on Dec. 15, 2005. The present application also claims priority to U.S. Provisional Application No. 60/834,643, filed on Aug. 1, 2006. The Present Application also claims priority to U.S. Provisional Application No. 60/840,826, filed on Aug. 29, 2006.

STATEMENT REGARDING FEDERALLY SPONSORED RESEARCH OR DEVELOPMENT

Not Applicable

BACKGROUND OF THE INVENTION

1. Field of the Invention

The present invention is related to health monitoring devices. More specifically, the present invention relates to eyewear capable of monitoring a user's real-time vital signs.

2. Description of the Related Art

There is a need to know how one is doing from a health perspective. In some individuals, there is a daily, even hourly, need to know one's health. The prior art has provided some devices to meet this need.

One such device is a pulse oximetry device. Pulse oximetry is used to determine the oxygen saturation of arterial blood. Pulse oximeter devices typically contain two light emitting diodes: one in the red band of light (660 nanometers) and one in the infrared band of light (940 nanometers). Oxyhemoglobin absorbs infrared light while deoxyhemoglobin absorbs visible red light. Pulse oximeter devices also contain sensors that detect the ratio of red/infrared absorption several hundred times per second. A preferred algorithm for calculating the absorption is derived from the Beer-Lambert Law, which determines the transmitted light from the incident light multiplied by the exponential of the negative of the product of the distance through the medium, the concentration of the solute and the extinction coefficient of the solute.

The major advantages of pulse oximetry devices include the fact that the devices are non-invasive, easy to use, allows for continuous monitoring, permits early detection of desaturation and is relatively inexpensive. The disadvantages of pulse oximetry devices are that it is prone to artifact, it is inaccurate at saturation levels below 70%, and there is a minimal risk of burns in poor perfusion states. Several factors can cause inaccurate readings using pulse oximetry including ambient light, deep skin pigment, excessive motion, fingernail polish, low flow caused by cardiac bypass, hypotension, vasoconstriction, and the like.

Chin et al., U.S. Pat. No. 6,018,673 discloses a pulse oximetry device that is positioned entirely on a user's nail to reduce out of phase motion signals for red and infrared wavelengths for use in a least squares or ratio-of-ratios technique to determine a patient's arterial oxygen saturation.

Smith, U.S. Pat. No. 4,800,495 discloses an apparatus for processing signals containing information concerning the pulse rate and the arterial oxygen saturation of a patient. Smith also discloses maintaining the position of the LEDs and detectors to prevent motion-artifacts from being produced in the signal.

Another method for using a pulse oximeter to measure blood pressure is disclosed in U.S. Pat. No. 6,616,613 to Goodman for a 'Physiological Signal Monitoring System'. The '613 patent discloses processing a pulse oximetry signal in combination with information from a calibrating device to determine a patient's blood pressure.

Chen et al, U.S. Pat. No. 6,599,251 discloses a system and method for monitoring blood pressure by detecting pulse signals at two different locations on a subjects body, preferably on the subject's finger and earlobe. The pulse signals are preferably detected using pulse oximetry devices.

Schulze et al., U.S. Pat. No. 6,556,852, discloses the use of an earpiece having a pulse oximetry device and thermopile to monitor and measure physiological variables of a user.

Malinouskas, U.S. Pat. No. 4,807,630, discloses a method for exposing a patient's extremity, such as a finger, to light of two wavelengths and detecting the absorbance of the extremity at each of the wavelengths.

Jobsis et al., U.S. Pat. No. 4,380,240 discloses an optical probe with a light source and a light detector incorporated into channels within a deformable mounting structure which is adhered to a strap. The light source and the light detector are secured to the patient's body by adhesive tapes and pressure induced by closing the strap around a portion of the body.

Tan et al., U.S. Pat. No. 4,825,879 discloses an optical probe with a T-shaped wrap having a vertical stem and a horizontal cross bar, which is utilized to secure a light source and an optical sensor in optical contact with a finger. A metallic material is utilized to reflect heat back to the patient's body and to provide opacity to interfering ambient light. The sensor is secured to the patient's body using an adhesive or hook and loop material.

Modgil et al., U.S. Pat. No. 6,681,454 discloses a strap that is composed of an elastic material that wraps around the outside of an oximeter probe and is secured to the oximeter probe by attachment mechanisms such as Velcro, which allows for adjustment after initial application without producing excessive stress on the spring hinge of the oximeter probe.

Diab et al., U.S. Pat. No. 6,813,511 discloses a disposable optical probe suited to reduce noise in measurements, which is adhesively secured to a patient's finger, toe, forehead, earlobe or lip.

Diab et al., U.S. Pat. No. 6,678,543 discloses an oximeter sensor system that has a reusable portion and a disposable portion. A method for precalibrating a light sensor of the oximeter sensor system is also disclosed.

Tripp, Jr. et al., U.S. Statutory Invention Registration Number H1039 discloses an intrusion free physiological condition monitor that utilizes pulse oximetry devices.

Hisano et al., U.S. Pat. No. 6,808,473, discloses a headphone-type exercise aid which detects a pulse wave using an optical sensor to provide a user with an optimal exercise intensity.

Mathews, U.S. Pat. No. 5,431,170 ("Mathews"), discloses a pulse responsive device, which has a pulse oximetry device (10) attached to a headband (12) and a separate read-out device (14) that may be attached to a glove and worn on the user's hand. Mathews discloses that the read-out device (14) has a digital display and an analogue display, however, Mathews provides no further detail.

Mault et al, U.S. Patent Application Publication Number 2002/0109600 ("Mault") discloses a smart activity monitor ("SAM") which is a pedometer based device which includes an electronic clock, a sensor, entry means for recording food consumption and exercise activities and a memory for storing such information. Mault fails to disclose the details of the display other than to mention that the SAM has a time display, an exercise display and a food display, with the exercise and food displays having a bar-graph style. Mault fails to disclose an optical sensor in detail, and only states that photo-plethysmography may be used to determine the heart rate by a sensor provided on the rear of a wrist mounted SAM.

Kopotic et al, U.S. Pat. No. 6,470,199, discloses a sock for positioning an optical probe.

Yasukawa et al., U.S. Pat. No. 5,735,800 ("Yasukawa"), discloses a wrist-worn device which is intended for limited motion about the user's wrist. Yasukawa discloses an optical sensor that uses a blue LED with a phototransistor in conjunction with an analog to digital converter to provide a digital signal to a data processing circuit.

In monitoring one's health there is a constant need to know how many calories have been expended whether exercising or going about one's daily routine. A calorie is a measure of heat, generated when energy is produced in our bodies. The amount of calories burned during exercise is a measure of the total amount of energy used during a workout. This can be important, since increased energy usage through exercise helps reduce body fat. There are several means to measure this expenditure of energy. To calculate the calories burned during exercise one multiplies the intensity level of the exercise by one's body weight (in kilograms). This provides the amount of calories burned in an hour. A unit of measurement called a MET is used to rate the intensity of an exercise. One MET is equal to the amount of energy expended at rest.

For example, the intensity of walking 3 miles per hour ("mph") is about 3.3 METS. At this speed, a person who weighs 132 pounds (60 kilograms) will burn about 200 calories per hour (60×3.3=198).

The computer controls in higher-quality exercise equipment can provide a calculation of how many calories are burned by an individual using the equipment. Based on the workload, the computer controls of the equipment calculate exercise intensity and calories burned according to established formulae.

The readings provided by equipment are only accurate if one is able to input one's body weight. If the machine does not allow this, then the "calories per hour" or "calories used" displays are only approximations. The machines have built-in standard weights (usually 174 pounds) that are used when there is no specific user weight.

There are devices that utilize a watch-type monitor to provide the wearer with heart rate as measured by a heartbeat sensor in a chest belt.

Further, MP3 Players have become a popular device for athletes to listen to music while working out. It would be desirable if athletes could get fitness information from their MP3 player.

Prior to the advent of MP3 players, Brink et al., U.S. Pat. No. 4,788,983 for a Pulse Rate Controlled Entertainment Device, discloses the use of an EKG device (electrodes connected to a module) combined with a portable radio such as a SONY® WALKMAN™ radio.

Hisano et al., U.S. Pat. No. 6,808,473 for an Exercise Promotion Device, And Exercise Promotion Method Employing The Same, discloses an exercise device that obtains a pulse rate and calculates an appropriate exercise level, and also contains music.

Burrell et al., U.S. Pat. No. 6,853,955 for a Portable Apparatus With Performance Monitoring And Audio Entertainment Features, discloses a device with an audio component that is preferably a MP3 player, a heart rate monitor component, and a GPS component.

The use of eye pieces with information displays is known in the prior art. More specifically, eye pieces with information displays heretofore devised and utilized for the purpose of displaying information by components located within one's eye glasses are known to consist basically of familiar, expected, and obvious structural configurations, notwithstanding the myriad of designs encompassed by the crowded prior art which has been developed for the fulfillment of countless objectives and requirements.

By way of example, in U.S. Pat. No. 4,354,744 to Bonomi discloses a frame for eyeglasses.

U.S. Pat. No. 4,526,483 to Zahn, III, discloses a heads up sports timer with electronic time display.

U.S. Pat. Nos. 4,751,691 and 4,867,551 both to Perera disclose an optical projection time-piece attachment for spectacles or combination thereof and a display projection optical system for spectacles or sunglasses.

U.S. Pat. No. 5,585,871 to Linden for a Multi-Function Display Apparatus discloses the use of a pulse detection means in a housing positioned on eyewear to determine the wearer's heart rate, however, the type of pulse detection means is undisclosed.

U.S. Pat. No. 6,431,705 to Linden for Eyewear Heart Rate Monitor discloses the use of electrodes in contact with the wearer's nose to determine the wearer's heart rate.

U.S. Pat. No. 6,769,767 to Swab et al. for Eyewear With Exchangeable Temples Housing A Transceiver Forming Ad Hoc Networks With Other Devices discloses the use of eyewear with a Bluetooth™ transceiver for establishing a network with other devices including a heart rate monitor.

U.S. Patent Publication 2005/0248718 to Howell et al., for Eyeglasses With Activity Monitoring discloses the use of an infrared LED and infrared detector in the temple of eyewear to provide a heart beat sensor.

Japanese Patent Publication Number 2001-245860 discloses the use of a pulse wave detection device embedded within eyeglasses for determining a wearer's pulse in which the pulse wave detection device is a light emitting element and alight receiving element.

U.S. Pat. No. 7,004,582 to Jannard et al., for Electronically Enabled Eyewear discloses eyewear with integrated speakers and means for wireless networking.

U.S. Patent Publication 2005/046790 to Jannard et al., for Speaker Mounts For Eyeglass With MP3 Player discloses eyewear with translatable speaker mounts.

U.S. Patent Publication 2004/0160573 to Jannard et al., for Wireless Interactive Headset discloses a headset with speakers, a microphone and an eyeglass frame.

U.S. Patent Publication 2005/0213026 to Da Pra, for Eyeglasses Preset For Connection To Cellular Telephones For Transmitting And Receiving Calls discloses eyewear with an integrated speaker, microphone and cable connection to a telephone.

U.S. Pat. No. 7,013,009 to Warren for Eyeglasses With Wireless Communication Features discloses an eyeglass frame with a microphone, transmitter, speaker, receiver and power source.

U.S. Patent Publication 2003/0179094 to Abreu, for Signal To Product Coupling discloses a monitoring device for obtaining biological readings from a facial sensor.

U.S. Pat. No. 5,830,139 to Abreu discloses in reference to FIG. 30 eyeglasses with a sensor in contact with a wearer's eye and means for transmitting a reading.

U.S. Pat. No. 7,041,063 to Abreu for a Noninvasive Measurement Of Chemical Substances discloses sensor worn on a user's face along with a radio frequency transmitter to detect physical and chemical parameters of the user.

The prior art has failed to provide a means for monitoring one's health that is accurate, easy to wear on one's body for extended time periods, allows the user to input information and control the output, and provides sufficient information to the user about the user's health. Thus, there is a need for a monitoring device that can be worn for an extended period and provide health information to a user.

BRIEF SUMMARY OF THE INVENTION

The present invention provides a solution to the shortcomings of the prior art. The present invention is accurate, comfortable to wear by a user on their face for extended time periods, allows for input and controlled output by the user, is light weight, and provides sufficient real-time information to the user about the user's health.

One aspect of the present invention is a monitoring device for monitoring the health of a user. The monitoring device includes eyewear, an optical sensor for generating a digital signal, a circuitry assembly embedded within a control device, a display member positioned on an exterior surface of the control device, and a control means disposed on the control member.

The eyewear preferably has the optical sensor integrated into its bridge. The optical sensor allows the user to track calories burnt during a set time period, monitor heart rate, blood oxygenation levels, distance traveled, target zones and/or optionally dynamic blood pressure.

Another aspect of the present invention is a method for monitoring a user's vital signs. The method includes generating a signal corresponding to the flow of blood through at least one facial of the user. The signal is generated from an optical sensor, which is integrated into eyewear. Next, the heart rate data of the user is generated from the signal. Next, the heart rate data of the user is processed for analysis of calories expended by the user and for display of the user's heart rate and other information. Next, the calories expended by the user, the user's heart rate or the user's blood oxygen saturation level are displayed on a display member on an exterior surface of a control member, which is controlled by the user using a control component.

Another aspect of the present invention is a system for monitoring the health of a user. The system includes a monitoring device and a handheld device. The monitoring device includes eyewear, an optical sensor, a digital music player, a controller and transmitting means. The eyewear has a lens or two lenses, temporal members and a nose support member. The optical sensor is integrated into the eyewear, either one of the temporal members or the nose support member. The optical sensor is capable generating a signal corresponding to the flow of blood through at least one facial artery of the user. The controller is connected to the eyewear and the digital music player. The transmitting means transmits a plurality of health information about the user. The handheld device or computer is capable of storing the plurality of health information transmitted by the monitoring device.

Yet another aspect of the present invention is a monitoring device for monitoring the health of a user. The monitoring device includes eyewear, measuring means, calculating means, display means and control means. The eyewear includes a lens, temporal members and a nose support. The measuring means measures blood flowing through at least one artery of the user and is disposed on the eyewear. The means for controlling the input information and the output of information displayed on the visually displaying means is positioned on the digital storage and processing device.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
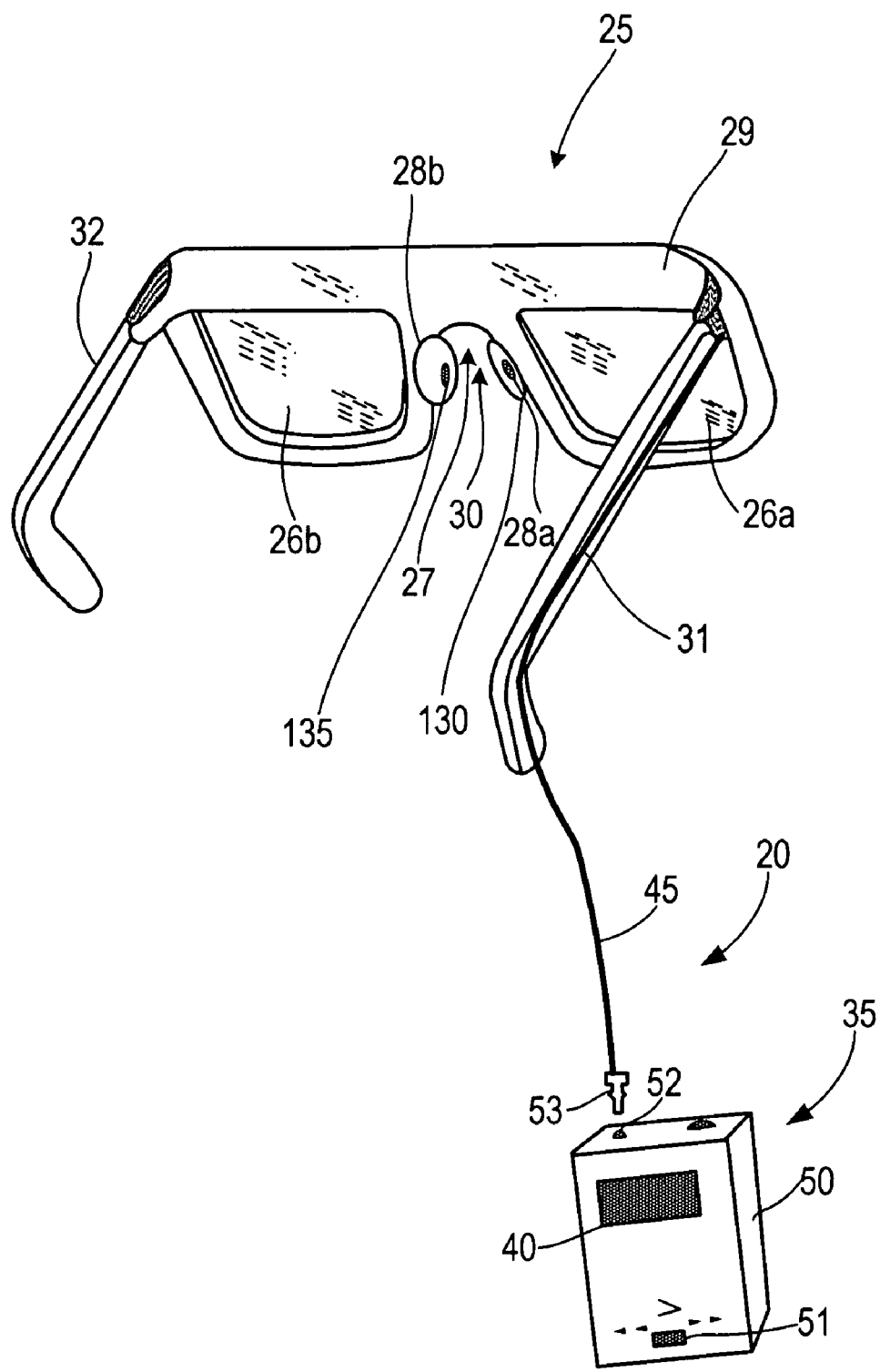
FIG. 1 is a schematic view of a preferred embodiment of a monitoring device including eyewear and a digital storage and processing device.
Figure 2:
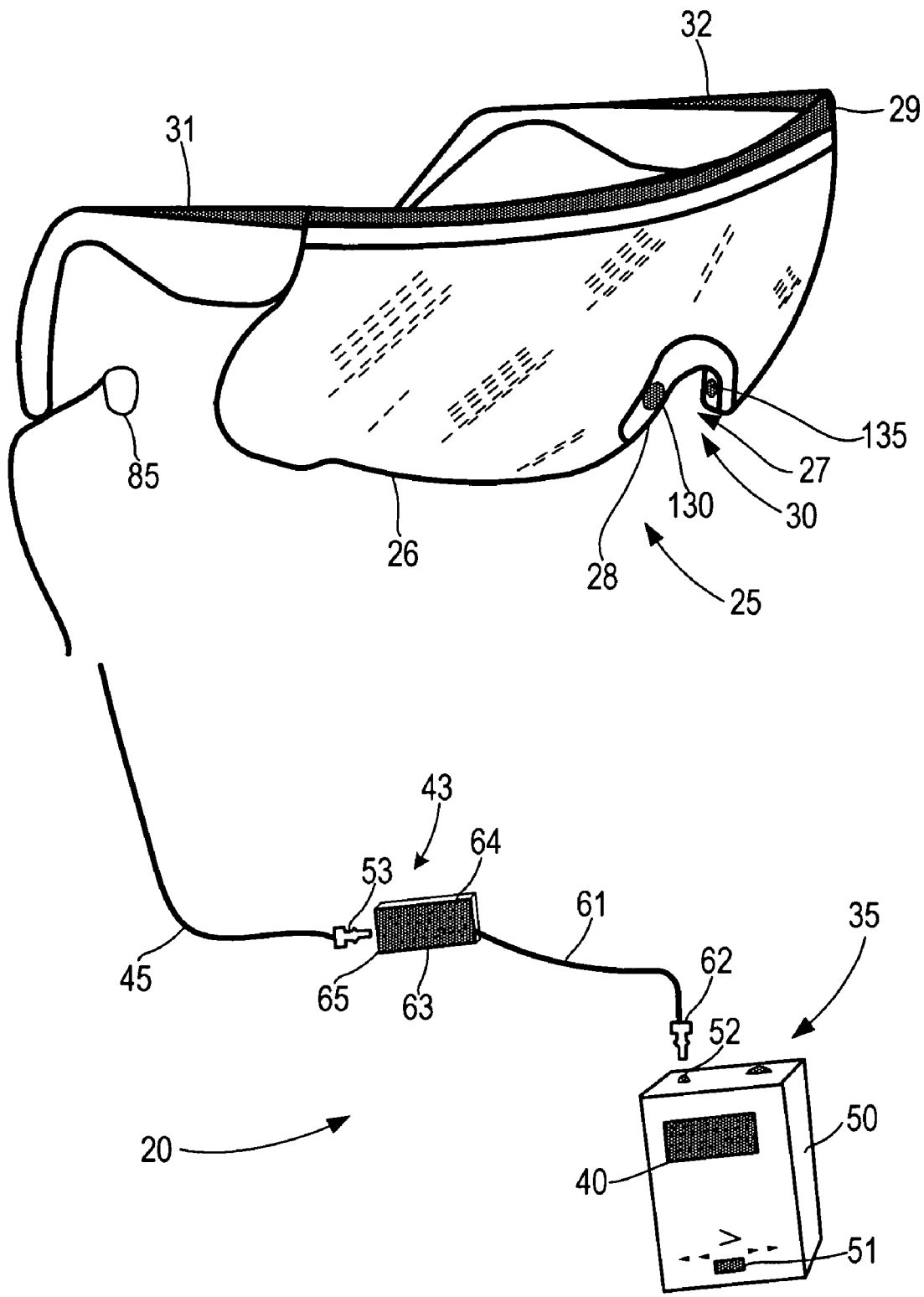
FIG. 2 is a schematic view of an alternative embodiment of a monitoring device including eyewear and a digital storage and processing device.
Figure 3:
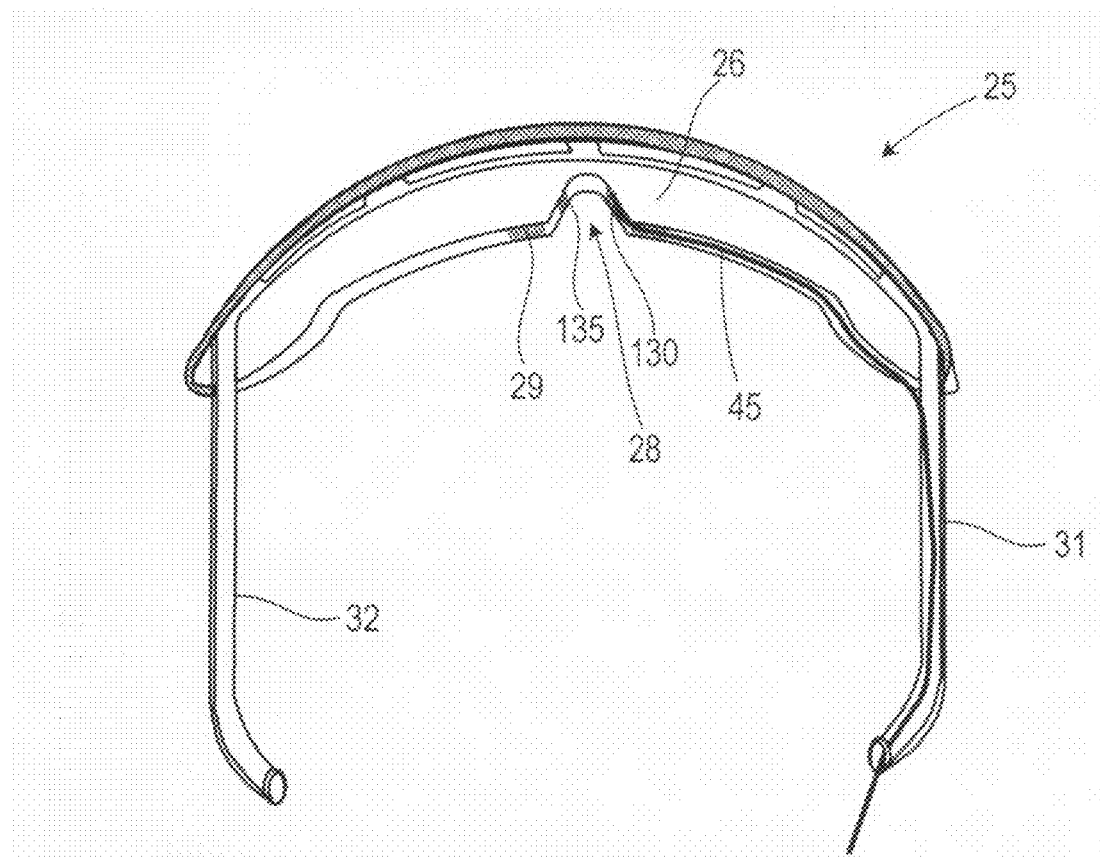
FIG. 3 is an isolated bottom plan view of eyewear utilized with the monitoring device.

As shown in FIGS. 1-3, a monitoring device is generally designated 20. In a preferred embodiment shown in FIG. 1, the monitoring device 20 comprises eyewear 25, an optical sensor 30, a digital storage and processing unit 35 and a connection cable 45. In an alternative embodiment shown in FIG. 2, the monitoring device 20 includes eyewear 25, an optical sensor 30, a digital storage and processing unit 35, a controller 43, a connection cable 45 and a controller cable 61.

The eyewear 25 is provided with a lens 26 or lenses 26a and 26b positioned in front of the eyes of the wearer within the user's forward field of vision. The lens 26 which includes the optical areas, may be made of various materials already known in the art including glass and plastic, and may be designed to provide protection from harmful electromagnetic waves such as the harmful UV rays of the sun. The embodiment of FIG. 2 is a wrap-around type eyewear 25, wherein the lens 26 may be formed from a single, unitary piece with the optical areas integrally formed thereon. The embodiment of FIG. 1 is constructed of multiple pieces. However, in other embodiments of the present invention as applied to other eyewear designs, the lens may be formed from multiple and/or separate pieces as known in the art.

Figure 1A:
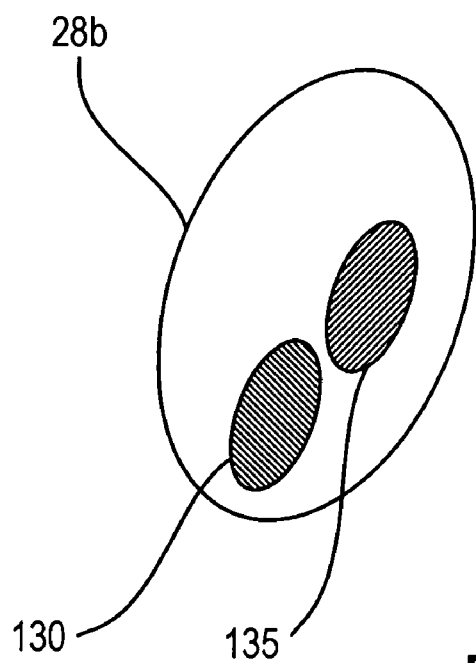
FIG. 1A is an isolated view of a preferred embodiment of the nose support of the eyewear of FIG. 1 containing the optical sensor.
Figure 1B:
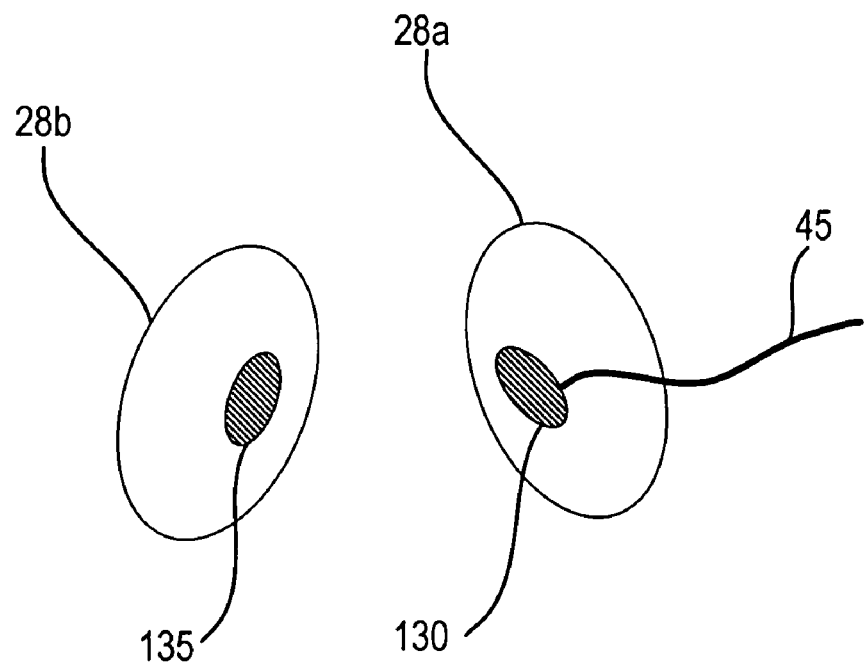
FIG. 1B is an isolated view of an alternative embodiment of the nose support of the eyewear of FIG. 1 containing the optical sensor.

The lens 26 includes a recessed nose area 27 including a nose support 28 (or 28a and 28b in FIG. 1) which allows the eyewear 25 to be supported on the user's face (not shown) in the manner conventionally known in the art. An optical sensor 30, as discussed below, is attached to the nose support 28. The optical sensor 30 has a light source 135 and a photodetector 130, which is connected to connection cable 45. An integral lens support portion 29 is provided on the eyewear 25 for supporting the lens 26 in the desired position within the user's forward field of vision. The connection cable 45 is preferably attached and/or integrated into the lens support position 29. As illustrated in FIG. 2, the lens support portion 29 is preferably integrally formed on the lens 26 from a similar transparent material so as to allow the user to see objects through the lens support portion 29. As shown in FIG. 1A, a reflective mode optical sensor 30 has the light source 135 and the photodetector 130 on nose support 28b. As shown in FIG. 1B, in an alternative embodiment, a transmission mode optical sensor 30 has the optical sensor 30 with the light source 135 in the nose support 28b and the photodetector 130 in the nose support 28a. In a preferred embodiment, the light source 135 and the photodetector 130 are integrated into the body of the nose support 28b, or nose supports 28a and 28b, so as to have little affect on the user, and to prevent adverse light from affecting the signal reading of the photodetector 130.

The eyewear 25 also preferably includes a first temporal member 31 attached to the lens support portion 29 on one end of the eyewear 25 and a second temporal member 32 attached to the lens support portion 29 on another end of the eyewear 25. The temporal members 31 and 32 allow the eyewear 25 to be worn by the wearer in a manner conventionally known in the art, and also allow for the connection cable 45 to be distributed rearward from the user's face. Both the first temporal member 31 and the second temporal member 32 may be provided with ear receiving portions which are curved to receive the top portions of the wearer's ears thereby retaining the eyewear 25 in position on the user's face. The temporal members 31 and 32 may be made from a similar material as the lens 26 thereby allowing the wearer to have peripheral vision through the temporal members while at the same time, providing protection from intense light and harmful radiation such as UV rays. To increase utility and portability, the first and second temporal members 31 and 32 may be hingedly attached by integral hinges to the lens support portion 29 thereby allowing the temporal members to be folded so as to make the eyewear 25 more compact.

Figure 4:
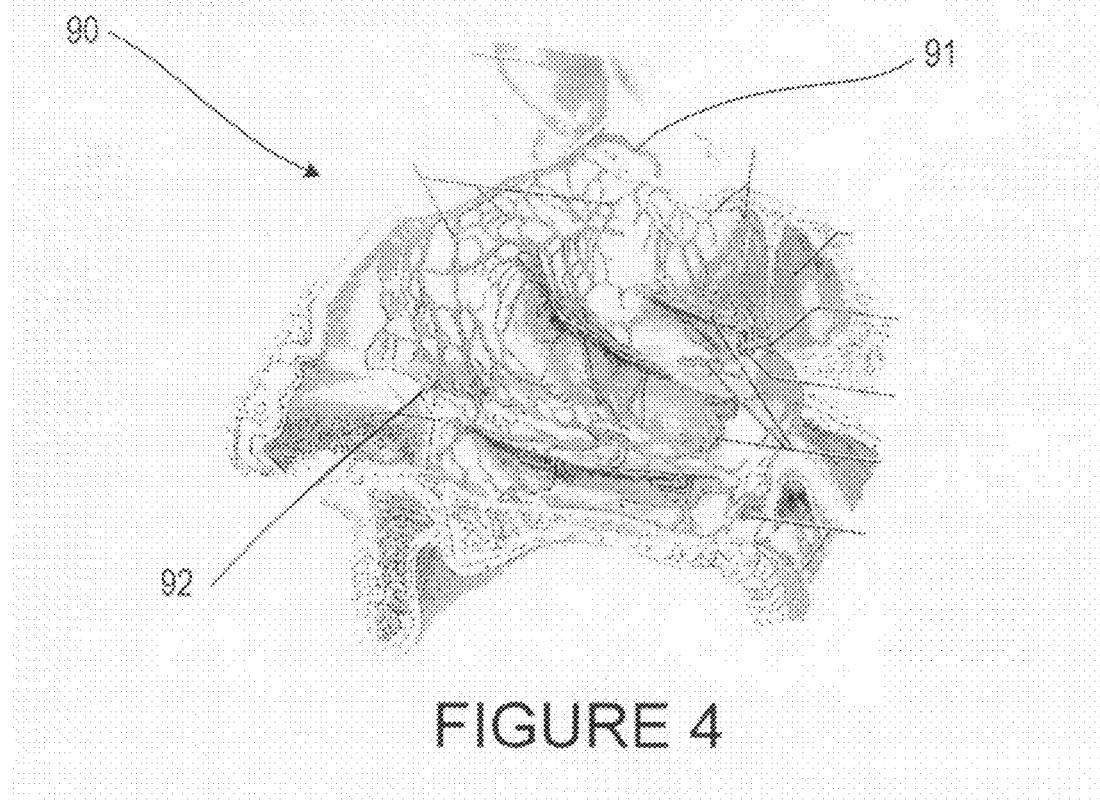
FIG. 4 is a schematic view of arteries within a human nose.

In a preferred embodiment, the optical sensor 30 is placed in contact with the nose 90 of the user and preferably in contact with the anterior ethmoidal artery of the walls of the nasal cavity 92, as shown in FIG. 4. Placement of the optical device 30 within the lens support portion 29 minimizes the motion artifacts, which interfere with the accuracy of the optical device, thereby providing a better signal reading for the photodetector 130.

Figure 7:
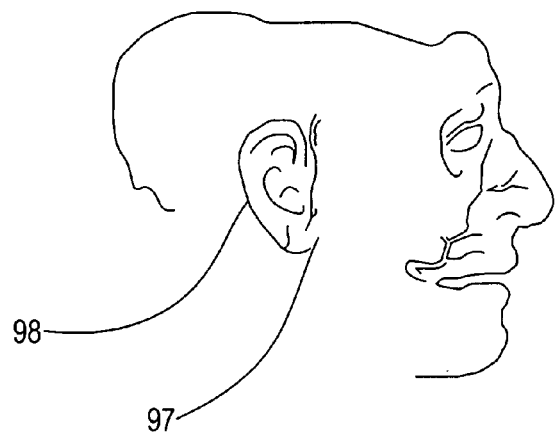
FIG. 7 is a schematic view of arteries within a human face.

In an alternative embodiment, the optical sensor 30 is positioned or embedded within one of the temporal members 31 or 32, using the reflective mode optical sensor 30. The optical sensor 30 is preferably in contact or in proximity to the superficial temporal artery 97 near the wearer's ear 98 as shown in FIG. 7.

Figure 16:
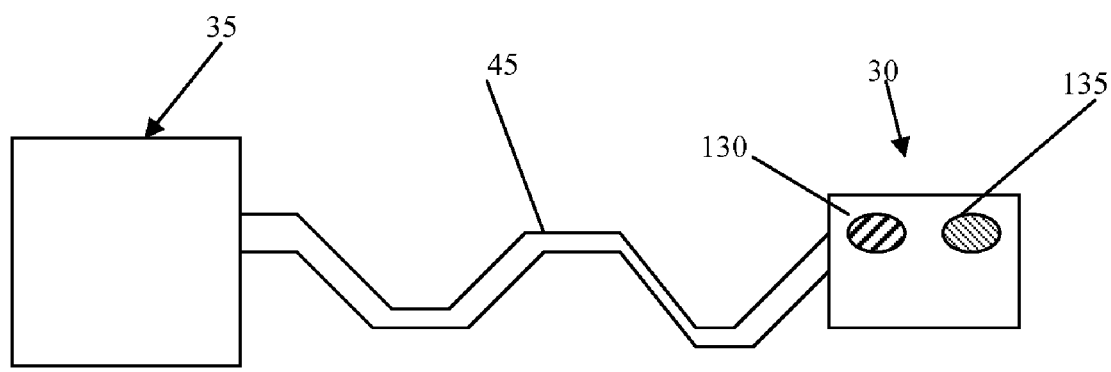
FIG. 16 is a schematic diagram of a connection of a processor to an optical sensor utilized by the present invention.

The connection cable 45 preferably is a bundle of several wires preferably including a power wire, an audio communication wire, a ground wire and a photodetection transmission wire. The photodetection transmission wire transmits the signal, preferably a digital signal, from the photodetector 130 to the digital storage and processing unit 35. Signal noise reduction means for the connection wire 45 are discussed below in reference to FIG. 16.

In a preferred embodiment, the optical sensor 30 is a single light emitting diode ("LED") 135 based on green light wherein the LED 135 generates green light ($\lambda$~500-600 nm), and a photodetector 130 detects the green light. Yet in an alternative embodiment, the optical sensor 30 is a photodetector 130 and a single LED 135 transmitting light at a wavelength of approximately 900 nanometers as a pulsed infrared LED. Yet further, the optical sensor is a combination of a green light LED and a pulsed infrared LED to offset noise affects of ambient light and sunlight. As the heart pumps blood through the arteries of the user, blood cells absorb and transmit varying amounts of the light depending on how much oxygen binds to the cells' hemoglobin. The photodetector 30, which is typically a photodiode, detects reflectance/transmission at the wavelengths (green, red or infrared), and in response generates a radiation-induced signal.

Alternatively, the optical sensor 30 is a pulse oximetry device with a light source 135 that typically includes LEDs that generate both red ($\lambda$~660 nm) and infrared ($\lambda$~900 nm) radiation. As the heart pumps blood through the user's arteries, blood cells absorb and transmit varying amounts of the red and infrared radiation depending on how much oxygen binds to the cells' hemoglobin. The photodetector 130, which is typically a photodiode, detects transmission at the red and infrared wavelengths, and in response generates a radiation-induced signal.

A preferred optical sensor 30 utilizing green light is a TRS1755 sensor from TAOS, Inc of Plano Tex. The TRS1755 comprises a green LED light source (567 nm wavelength) and a light-to-voltage converter. The output voltage is directly proportional to the reflected light intensity. Another preferred photodetector 130 is a light-to-voltage photodetector such as the TSL260R and TSL261, TSL261R photodetectors available from TAOS, Inc of Plano Tex. Alternatively, the photodetector 130 is a light-to-frequency photodetector such as the TSL245R, which is also available from TAOS, Inc. The light-to-voltage photodetectors have an integrated transimpedance amplifier on a single monolithic integrated circuit, which reduces the need for ambient light filtering. The TSL261 photodetector preferably operates at a wavelength greater than 750 nanometers, and optimally at 940 nanometers, which would preferably have a LED that radiates light at those wavelengths.

The digital storage and processing unit 35 is preferably a MP3 player such as the IPOD™ MP3 player from Apple Computer of Cupertino Calif., or other similar devices available from Hewlett Packard or Dell Computer. The use of a MP3 player with the monitoring device 20 allows for the user to listen to music or other audio information through earphone 85 while monitoring the user's health parameters with the optical device 30. Alternatively, the digital storage device 35 is a PDA such as a BLACKBERRY™ device from Research In Motion Company, or a SMARTPHONE™ TREO™ device from Palm Company.

Figure 10:
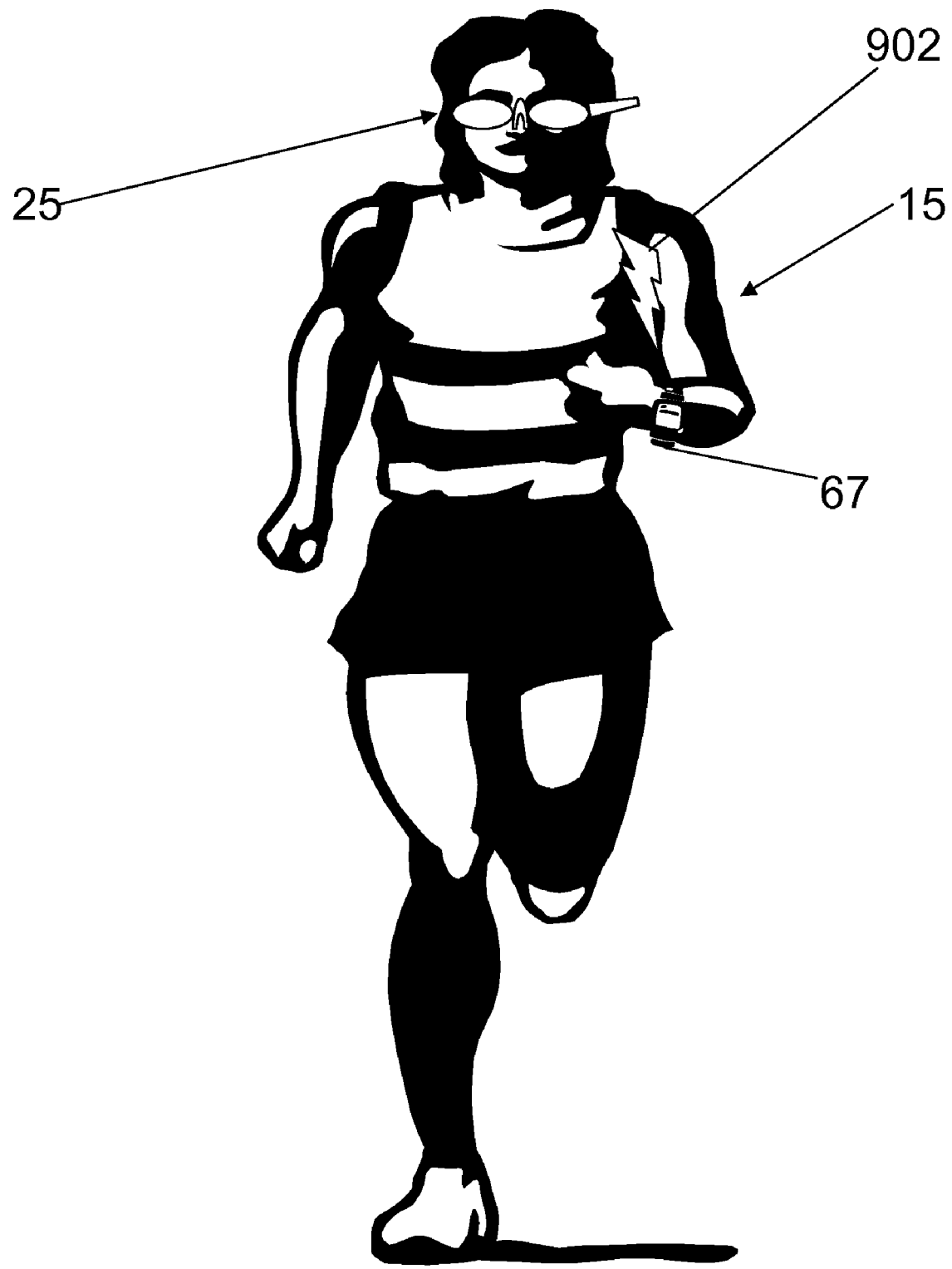
FIG. 10 is an illustration of a runner wearing an alternative embodiment of the monitoring device including eyewear and a watch.
Figure 11:
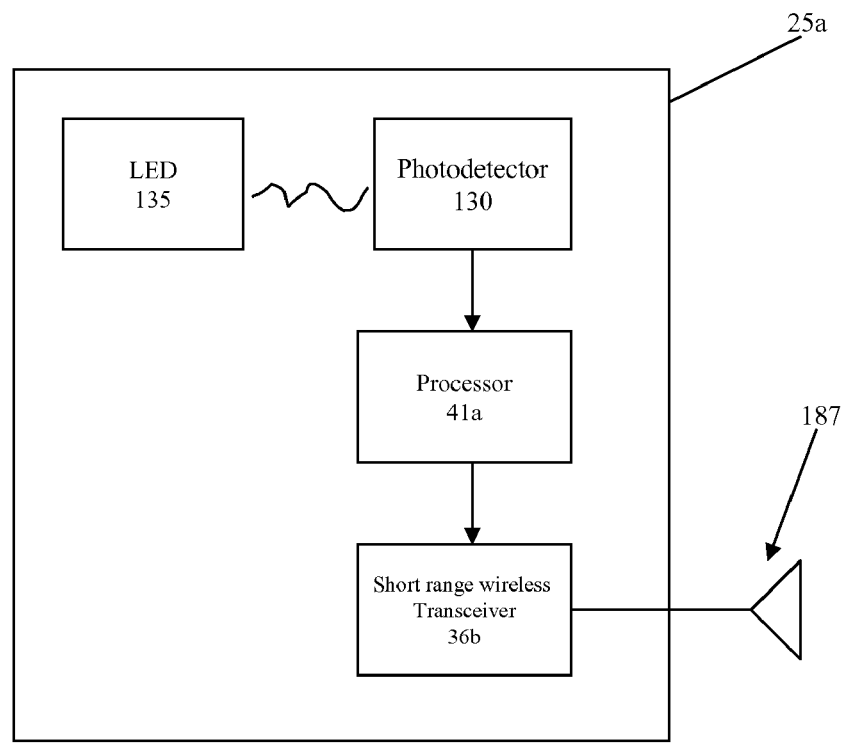
FIG. 11 is a block diagram of the electrical components utilized with the eyewear of the monitoring device of FIG. 10.

Yet further, in reference to FIG. 10, the digital storage device is a watch 67 which receives a wireless transmission 902 from the circuitry on the eyewear 25 while worn on an arm of the user 15. The watch is capable of displaying the user's real-time vital signs on a display member on the face of the watch. As shown in FIG. 11, the eyewear circuitry 25a comprises the LED 135 and photodetector 130, a processor 41a, a short range wireless transceiver 36b and an antenna 187. The radiation induced signal from the photodetector 130 is sent to the processor 41a for processing. The processed information is sent by the short range wireless transceiver 36b to the watch 67 via the antenna 187.

As shown in FIGS. 1 and 2, the digital storage and processing unit 35 preferably includes a housing 50, a display screen 40, a function control 51 and a connection cable receptor 52. Within the housing 50 of the digital storage and processing unit 35 are preferably a microprocessor, a memory, a battery, a communication interface, and an earphone interface. The microprocessor can process the data to display the health parameters such as a pulse rate, blood oxygenation levels, calories expended by the user of a pre-set time period, target zone activity, time and dynamic blood pressure. The memory can store the health parameters. The memory may also store digital music.

The display screen of the digital storage and processing unit 35 is preferably a liquid crystal display ("LCD"). Alternatively, the display screen 40 is a light emitting diode ("LED"), a combination of a LCD and LED, or other similar display device. As shown in FIG. 4, the display screen 40 displays the health parameters of the user.

The digital storage and processing unit 35 may optionally have a short range wireless transceiver for transmitting processed information processed from the digital storage and processing unit 35 to a handheld device 150 or a computer, not shown. The short-range wireless transceiver is preferably a transmitter operating on a wireless protocol, e.g. BLUETOOTH™, part-15, or 802.11. "Part-15" refers to a conventional low-power, short-range wireless protocol, such as that used in cordless telephones. The short-range wireless transmitter (e.g., a BLUETOOTH™ transmitter) receives information from the microprocessor and transmits this information in the form of a packet through an antenna. The external laptop computer or hand-held device 150 features a similar antenna coupled to a matched wireless, short-range receiver that receives the packet. In certain embodiments, the handheld device 150 is a cellular telephone with a BLUETOOTH™ circuit integrated directly into a chipset used in the cellular telephone. In this case, the cellular telephone may include a software application that receives, processes, and displays the information. The secondary wireless component may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof. Alternatively, the handheld device 150 is a pager or PDA.

Alternatively, the digital storage and processing unit 35 can connect through use of a wire to a computer 150 through a USB or FIREWIRE ports, especially if a MP3 player is utilized as the digital storage and processing unit 35.

In an alternative embodiment shown in FIG. 2, the controller 43 is connected between the eyewear 25 and the digital storage and processing device 35. A controller cable 61 connects the controller 43 to the digital storage and processing unit 35 by placing a controller plug 62 into the cable receptor 52. The eyewear 25 is connected to the controller 43 by the connection cable 45. In one embodiment, the controller 43 functions as converter to convert the digital signal from the photodetector 130 into a format that is usable by the digital storage and processing unit 35.

Alternatively, the controller receives the signal from the photodetector 130 and processes the information using a microprocessor within a housing 65 of the controller 43. The controller 43 also preferably has function controls 63 and a display screen 64. The user uses the function controls 63 to change the health information displayed on the display screen 64. In this embodiment, the controller 43 would receive and process all of the information from the optical device 30 to generate the plurality of health parameters. The controller optionally can display the plurality of health parameters on its display screen 64. In such an alternative embodiment, the controller 43 could control the audio feed of information from the digital storage and processing device 35. The controller 43 could also operate with other portable audio devices such as CD players, walkman style cassettes, minidisk players.

The monitoring device 20 optionally could utilize a pedometer to measure distance traveled. The pedometer could be integrated with the controller 43 or the digital storage and processing device.

The display member 40 is preferably a light emitting diode ("LED"). Alternatively, the display member 40 is a liquid crystal display ("LCD") or other similar display device. The display member 40 is preferably an LED array which preferably has seven rows and thirteen columns. The LED array allows for each column to be illuminated separately thereby giving the appearance of a moving display. For example, if the term "200 calories expended" is displayed on the display member 40, the "2" of the "200" would preferably first appear in a first column and then subsequently in each of the other columns, from the right-most column to the left-most column thereby giving the appearance of the term scrolling along the display member 40. The terms or words alternatively scroll from left to right. Still alternatively, all of the columns are illuminated at once or all flash in strobe like manner. Further, a real-time pulse waveform of the user is displayed as the default on the display member 40. Those skilled in the pertinent art will recognize alternative methods of displaying information on the display member 40 without departing from the scope and spirit of the present invention.

Figure 5:
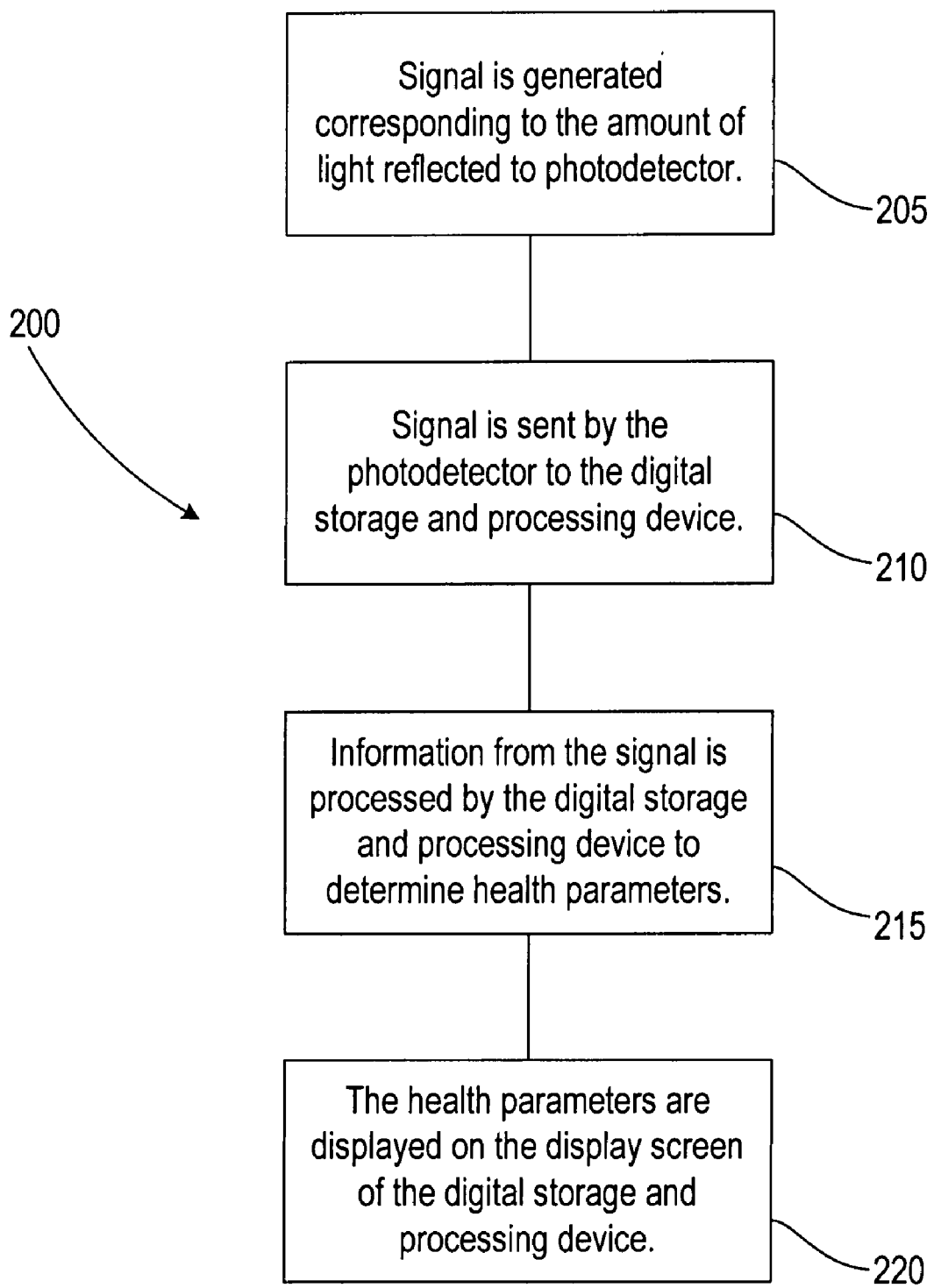
FIG. 5 is a flow chart of a general method of monitoring.

As shown in FIG. 5, a general method is indicated as 200. At block 205, the light source 135 of the optical device 30 transmits light at the nose 90 of the user. The photo-detector 130 detects the light. The pulse rate is determined by the signals received by the photo-detector 130. The ratio of the fluctuation of the red and/or infrared light signals is used to calculate the blood oxygen saturation level of the user.

At block 210, a signal is sent to digital storage and processing unit 35 for creation of blood oxygenation level, pulse rate, signal strength bar graph, plethysmogram and/or status bits data. At block 215, a microprocessor on the digital storage and processing device 35 further processes the information to display pulse rate, blood oxygenation levels, calories expended by the user of a pre-set time period, target zones of activity, time and/or dynamic blood pressure. At block 220, the information is displayed on the display screen 40 of the digital storage and processing unit 35.

An alternative method includes the light source 135 of the optical device 30 transmitting light at the nose 90 of the user. The photo-detector 130 detects the light. The pulse rate is determined by the signals received by the photo-detector 130. The ratio of the fluctuation of the red and/or infrared light signals is used to calculate the blood oxygen saturation level of the user. Then, the signal is sent to the controller 43 to be converted into a usable format for the digital storage and processing unit 35. Then, the signal is sent from the controller 43 to the digital storage and processing unit 35. Then, the information contained in the signal is processed by the microprocessor on the digital storage and processing unit 35 to generate blood oxygenation level, pulse rate, signal strength bar graph, plethysmogram and/or status bits data. Further processing of the information is performed by the microprocessor to generate pulse rate, blood oxygenation levels, calories expended by the user of a pre-set time period, target zones of activity, time and dynamic blood pressure. Then, the information is displayed on the display screen 40 of the digital storage and processing unit 35.

Another alternative method includes the light source 135 of the optical device 30 transmitting light at the nose 90 of the user. The photo-detector 130 detects the light. The pulse rate is determined by the signals received by the photo-detector 130. The ratio of the fluctuation of the red and/or infrared light signals is used to calculate the blood oxygen saturation level of the user. Then, the signal is sent to the controller 43 to be converted into a usable format for the digital storage and processing unit 35. The information contained in the signal is processed by the microprocessor on the controller 43 to generate blood oxygenation level, pulse rate, signal strength bar graph, plethysmogram and/or status bits data. Further processing of the information is performed by the microprocessor to generate pulse rate, blood oxygenation levels, calories expended by the user of a pre-set time period, target zones of activity, time and/or dynamic blood pressure. Then, a health information signal is sent from the controller 43 to the digital storage and processing unit 35. Then, the information is displayed on the display screen 40 of the digital storage and processing unit 35.

The monitoring device 20 may also include controls to search for information to be displayed on the display screen, to set time periods for measurement of calories or the like, and to reset the monitoring device 20. Further, a battery, not shown, is utilized to power the various components of the monitoring device 20.

The monitoring device 20 may also be able to download the information to a computer for further processing and storage of information. The download may be wireless or through cable connection. The information can generate an activity log or a calorie chart.

A general method of using the monitoring device 20 begins with the light source 135 transmitting red and/or infrared light through a nose of the user. The photo-detector 130 detects the light. The pulse rate is determined by the signals received by the photo-detector 130. The ratio of the fluctuation of the red and/or infrared light signals is used to calculate the blood oxygen saturation level of the user. An optical sensor 30 with a photodetector 130 and single LED 135 is preferably utilized. Alternatively, a pulse oximetry device with two LEDs and a photodetector is utilized. Next, this information is sent to pulse oximetry board in the digital storage and processing device 35 for creation of blood oxygenation level, pulse rate, signal strength bargraph, plethysmogram and/or status bits data. Next, the microprocessor further processes the information to display pulse rate, blood oxygenation levels, calories expended by the user of a pre-set time period, target zones of activity, time and dynamic blood pressure. Next, the information is displayed on the display member 40.

In a preferred embodiment, the device 35 has multiple control buttons. The control buttons are preferably positioned in relation to the display member 40 to allow the user immediate visual feedback of the user's inputted information. The middle control button preferably activates the device 20, allows for the user's personal data to be entered and for choices to be selected by the user. The left button preferably allows for the user's calories burned to be displayed on the display member 40 and for the activity to be reset. The right button preferably allows for other fitness monitoring features to be displayed.

To activate, the middle button is depressed for preferably 0.5 seconds and then released. The display member will appear with a current pulse of the user and a calories burned display. The microprocessor preferably stores the calories burned and accumulates the values for a daily calories burned value and a total calories burned value until the activity is reset.

To enter the user's personal data, the middle button is depressed for 2 seconds and then released. The user will enter gender, age, mass, height and resting heart rate. Entering the data entails pushing the middle button to select a category (gender, age, . . . ) and then pushing the right or left button to scroll through the available options or to enter a value (e.g. age of the user). The middle button is pressed again to save the entry. This process is preformed until the user's has entered all of the data that the user wishes to enter into the microprocessor. The display member 40 will then display a heart rate and current calories burned value. A preset resting heart rate for men and women is preferably stored on the microprocessor, and used as a default resting heart rate. However, the user may enter their own resting heart rate value if the user is aware of that value. To access daily calories, the left button is pushed by the user and the display member 40 will illustrate the value for daily calories burned by the user. If the left button is pushed again, the value for total calories burned by the user will be displayed on the display member 40. The left button is pushed again to return to a heart rate value on the display member 40.

The right button is pushed to scroll through the choices of other output values, which comprises: basal metabolic rate; average heart rate; minimum heart rate; maximum heart rate; fat burn heart rate exercise target zone; cardio burn heart rate exercise target zone; and, summary of daily calories burned. The basal metabolic rate (displayed as "BMR") is an estimate of the total calories burned by the user in one day without exercise, and is based on the user inputted personal data. The average heart rate (displayed as "avHR") is the average heart rate of the user between resets, and is an overall indicator of fitness. The lower the average heart rate, the healthier the heart. The average heart rate is also a measure of the effectiveness of the exercise program employed by the user since a decrease in the average heart rate of the user will indicate the user's fitness has improved. The minimum heart rate (displayed as "mnHR") of the user is typically measured during sleep and periods of relaxation. The maximum heart rate (displayed as "mxHR") is typically measured during intense workouts. The fat burn heart rate exercise target zone (displayed as "fatB") displays a low and high range for the heart rate of the user to optimize fat burning during exercise. The cardio burn heart rate exercise target zone provides a high and low range for the heart rate of the user to optimize cardio conditioning during exercise. The summary of daily calories burned (displayed as "cal") displays the daily calories burned by the user.

The microprocessor can use various methods to calculate calories burned by a user. One such method uses the Harris-Benedict formula. Other methods are set forth at www.un-u.edu/unupress/food2/, which relevant parts are hereby incorporated by reference. The Harris-Benedict formula uses the factors of height, weight, age, and sex to determine basal metabolic rate (BMR). This equation is very accurate in all but the extremely muscular (will underestimate calorie needs) and the extremely overweight (will overestimate caloric needs) user.

The equations for men and women are set forth below:

Men: BMR=66+(13.7×mass (kg))+(5×height (cm))−(6.8×age (years))

Women: BMR=655+(9.6×mass)+(1.8×height)−(4.7×age)

The calories burned are calculated by multiplying the BMR by the following appropriate activity factor: sedentary; lightly active; moderately active; very active; and extra active.

Sedentary=BMR multiplied by 1.2 (little or no exercise, desk job)

Lightly active=BMR multiplied by 1.375 (light exercise/sports 1-3 days/wk)

Moderately Active=BMR multiplied by 1.55 (moderate exercise/sports 3-5 days/wk)

Very active=BMR multiplied by 1.725 (hard exercise/sports 6-7 days/wk)

Extra Active=BMR multiplied by 1.9 (hard daily exercise/sports & physical job or 2×day training, marathon, football camp, contest, etc.)

Various target zones may also be calculated by the microprocessor. These target zones include: fat burn zone; cardio zone; moderate activity zone; weight management zone; aerobic zone; anaerobic threshold zone; and red-line zone.

Fat Burn Zone=(220−age)×60% & 70%

An example for a thirty-eight year old female:

(220−38)×0.6=109

(220−38)×0.7=127

Fat Burn Zone between 109 to 127 heart beats per minute.

Cardio Zone=(220−your age)×70% & 80%

An example for a thirty-eight year old female:

(220−38)×0.7=127

(220−38)×0.8=146

Cardio zone is between 127 & 146 heart beats per minute.

Moderate Activity Zone, at 50 to 60 percent of your maximum heart rate, burns fat more readily than carbohydrates. That is the zone one should exercise at if one wants slow, even conditioning with little pain or strain.

Weight Management Zone, at 60 to 70 percent of maximum, strengthens ones heart and burns sufficient calories to lower one's body weight.

Aerobic Zone, at 70 to 80 percent of maximum, not only strengthens one's heart but also trains one's body to process oxygen more efficiently, improving endurance.

Anaerobic Threshold Zone, at 80 to 90 percent of maximum, improves one's ability to rid one's body of the lactic-acid buildup that leads to muscles ache near one's performance limit. Over time, training in this zone will raise one's limit.

Red-Line Zone, at 90 to 100 percent of maximum, is where serious athletes train when they are striving for speed instead of endurance.

EXAMPLE ONE

Female, 30 yrs old, height 167.6 centimeters, weight 54.5 kilograms.

The BMR=655+523+302−141=1339 calories/day.

The BMR is 1339 calories per day. The activity level is moderately active (work out 3-4 times per week). The activity factor is 1.55. The TDEE=1.55×1339=2075 calories/day. TDEE is calculated by multiplying the BMR of the user by the activity multiplier of the user.

A system may use the heart rate to dynamically determine an activity level and periodically recalculate the calories burned based upon that factor. An example of such an activity level look up table might be as follows:

Activity/Intensity Multiplier Based on Heart Rate

Sedentary=BMR×1.2 (little or no exercise, average heart rate 65-75 bpm or lower)

Lightly active=BMR×3.5 (light exercise, 75 bpm-115 bpm)

Mod. active=BMR×5.75 (moderate exercise, 115-140 pm)

Very active=BMR×9.25 (hard exercise, 140-175 bpm)

Extra active=BMR×13 (175 bpm−maximum heart rate as calculated with MHR formula)

For example, while sitting at a desk, a man in the above example might have a heart rate of between 65 and 75 beats per minute (BPM). (The average heart rate for an adult is between 65 and 75 beats per minute.) Based on this dynamically updated heart rate his activity level might be considered sedentary. If the heart rate remained in this range for 30 minutes, based on the Harris-Benedict formula he would have expended 1.34 calories a minute×1.2 (activity level)×30 minutes, which is equal to 48.24 calories burned.

If the man were to run a mile for 30 minutes, with a heart rate ranging between 120 and 130 bpm, his activity level might be considered very active. His caloric expenditure would be 1.34 calories a minute×9.25 (activity level)×30 minutes, which is equal to 371.85.

Another equation is weight multiplied by time multiplied by an activity factor multiplied by 0.000119.

Figure 6:
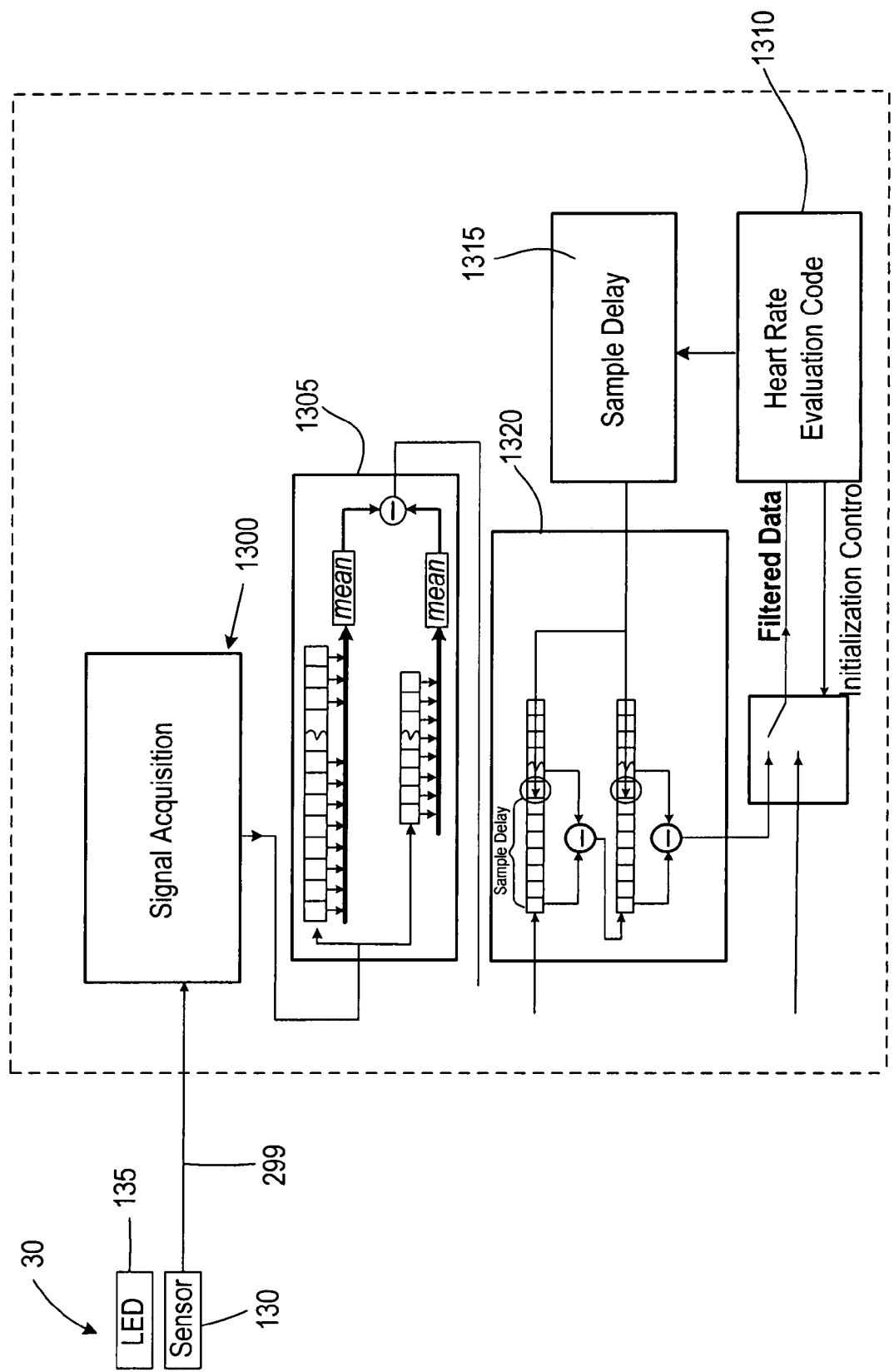
FIG. 6 is a schematic flow chart of a method of signal processing.
Figure 8:
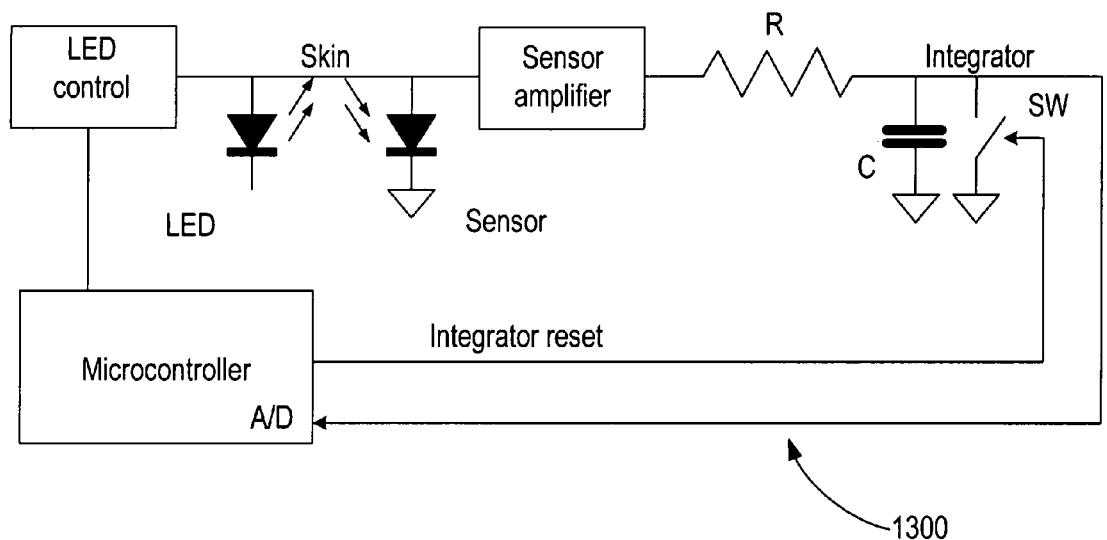
FIG. 8 is a flow chart of a signal acquisition step of the flow chart of FIG. 10.
Figure 9:
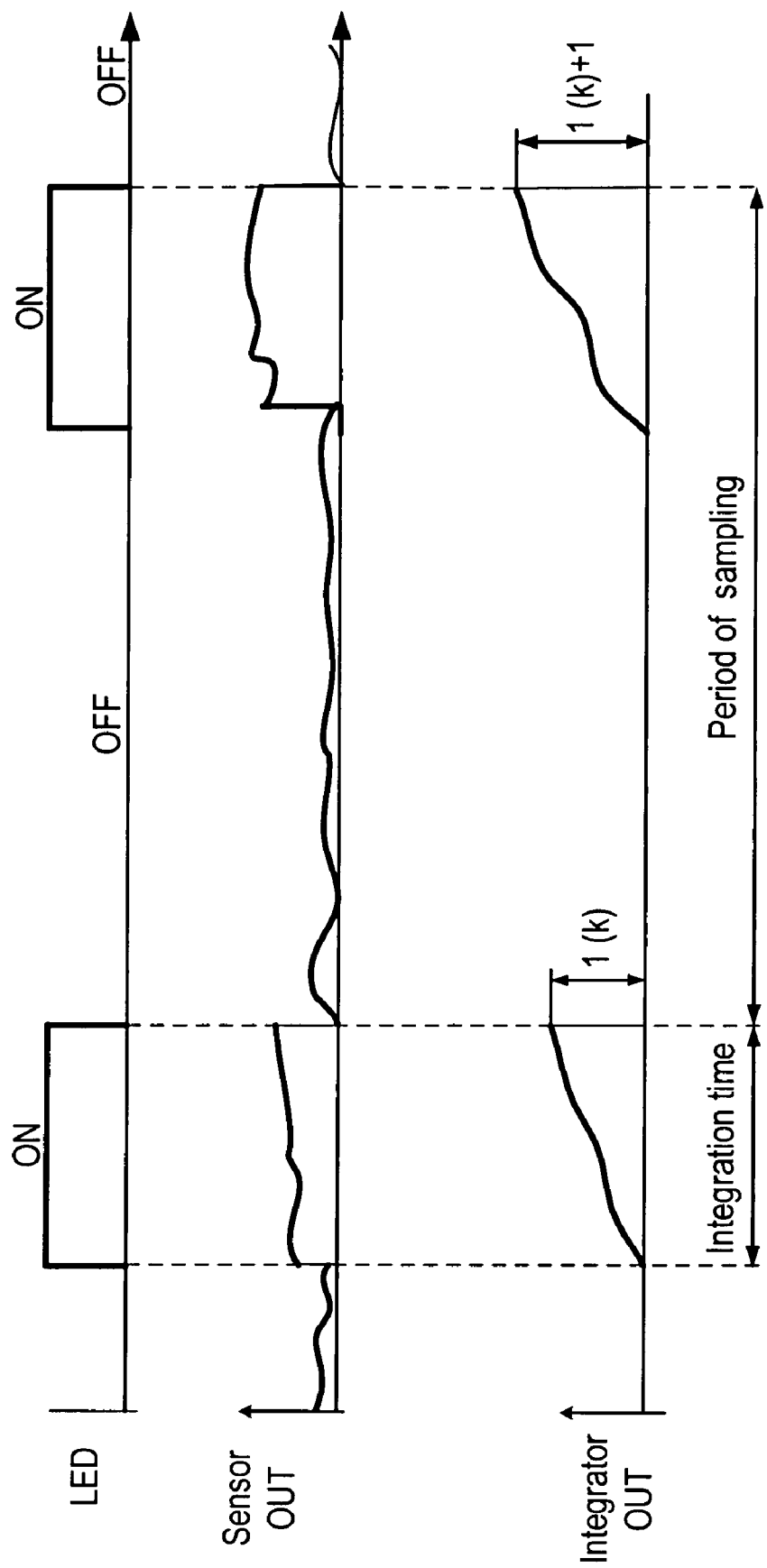
FIG. 9 is an illustration of the waveforms of data sampling.

FIG. 6 illustrates a flow chart of a signal processing method of the present invention. As shown in FIG. 6, the photodetector 130 of the optical sensor 30 receives light from the light source 135 while in proximity to the user's nose 90 (reference to FIG. 4) or ear 98 (reference to FIG. 7). In a preferred embodiment, the optical sensor 30 is a TRS1755 which includes a green LED light source (567 nm wavelength) and a light-to-voltage converter. The output voltage is directly proportional to the reflected light intensity. The signal 299 is sent to the microprocessor 41. At block 1300, the signal acquisition is performed, which is shown in greater detail in FIG. 8. In the pulse mode the LED 135 is periodically activated for short intervals of time by a signal from the microcontroller. The reflected pulse of light is received by the sensor, with the generation of a voltage pulse having an amplitude proportional to the intensity of the reflected light. When the LED is activated, the switch, SW, is open by the action of the control signal from the microcontroller, and the capacitor, C, integrates the pulse generated from the sensor by charging through the resistor R. Immediately prior to deactivation of the LED, the analog-to-digital converter acquires the value of the voltage integrated across the capacitor, C. The analog-to-digital converter generates a data sample in digital form which is utilized by the microcontroller for evaluation of the heart rate the wearer. Subsequent to the sample being acquired by the analog-to-digital converter, the LED is deactivated and the capacitor, C, is shortcut by switch, SW, to reset the integrator, RC. This states remains unchanged for a given time interval after which the process is repeated, which is illustrated in FIG. 9. A noise reduction and power reduction process is discussed below in reference to FIGS. 13 and 14.

At block 1305, a band pass filter is implemented preferably with two sets of data from the analog-to-digital converter. At block 1305, an average of the values of data samples within each of a first set of samples is calculated by the microprocessor. For example, the values of data samples within forty-four samples are summed and then divided by forty-four to generate an average value for the first set of samples. Next, an average of the values of data samples within a second set of samples is calculated by the microprocessor. For example, the values of data samples within twenty-two samples are summed and then divided by twenty-two to generate an average value for the second set of samples. Preferably, the second set of samples is less than the first set of samples. Next, the average value of the second set of samples is subtracted from the average value for the first set of samples to generate a first filtered pulse data value.

At block 1310, the filtered pulse data value is processed using a heart rate evaluation code to generate a first heart rate value. In a preferred method, the heart rate evaluation code obtains the heart rate by calculating the distance between crossing points of the voltage through zero. Once the first heart rate value is known, then an adaptive resonant filter is utilized to generate a filtered second heart rate value by attenuating interference caused by motion artifacts. At block 1315, a sample delay is computed as the period of evaluated heart rate divided by two.

At block 1320, preferably a two cascade adaptive resonant filter generates a second filtered pulse data value which is processed at block 1310 using the heart rate evaluation code to generate a second heart rate value. Those skilled in the pertinent art will recognize that three, four, or more, cascade adaptive resonant filters may be utilized in generating the second filtered pulse data value. Essentially, the highest and lowest values are disregarded in calculating the filtered second heart rate value. Alternatively, a phase is established and any values outside of the phase are disregarded in calculating the second heart rate value. The filtering is preferably continued during the use of the monitor thereby further refining the heart rate value of the user.

Figure 12:
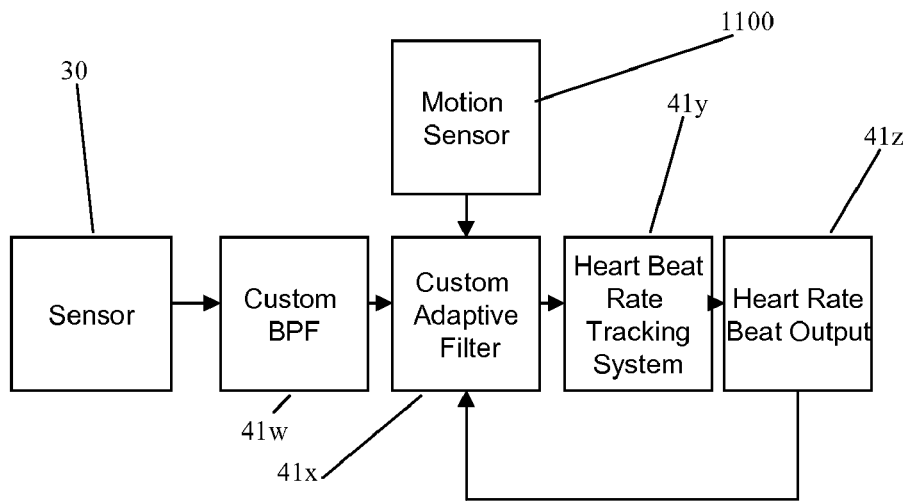
FIG. 12 is a flow chart of a signal processing noise reduction method alternatively utilized with the signal processing method of the present invention.

As shown in FIG. 12, a motion sensor 1100 is included in an alternative embodiment to assist in identifying motion noise and filtering the noise from the signal sent by the sensor 30. The motion sensor 1100, such as an accelerometer, is integrated into the circuitry and software of the monitoring device 20. As the motion sensor detects an arm swinging, the noise component is utilized with the signal processing noise filtering techniques to provide additional filtering to remove the noise element and improve the accuracy of the monitoring device 20. More specifically, the signal from the sensor 30 is transmitted to the processor where a custom blood pressure filter 41w processes the signal which is further processed at by custom adaptive filter 41x before being sent to a heart beat tracking system 41y and then transmitted to a heart rate beat output 41z. The heart rate beat output 41z provides feedback to the custom adaptive filter 41x which also receives input from the motion sensor 1100.

Figure 13:
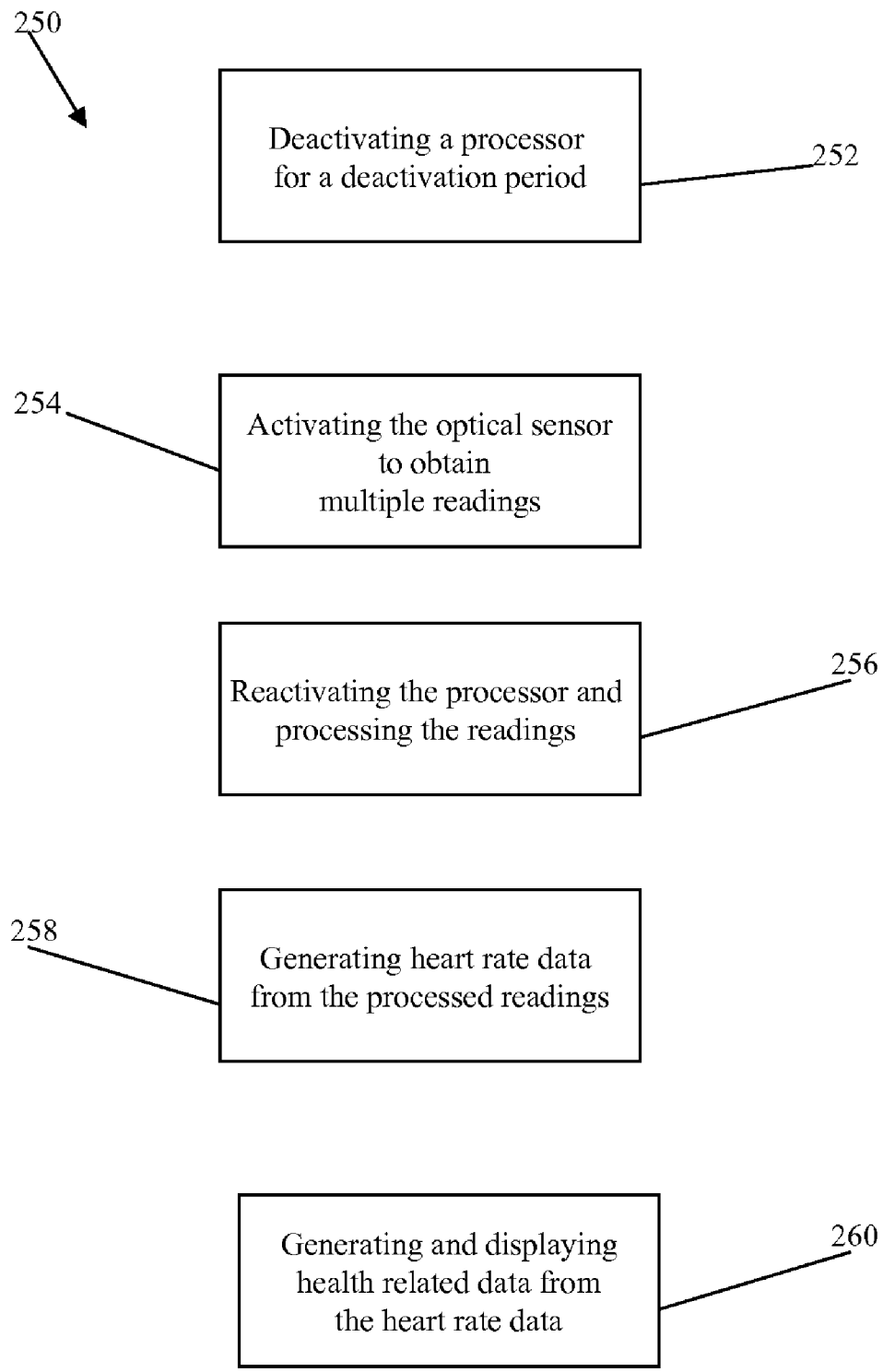
FIG. 13 is a flow chart of a noise reduction method of the present invention.

FIG. 13 illustrates a noise reduction method of the present invention. Due to the desire to minimize power consumption of the monitoring device 20, and achieve very accurate signal measurements using the optical sensor 30, the present invention preferably utilizes the method 250 illustrated in FIG. 13. At block 252, the processor 41 is deactivated for a deactivation period in order to conserve power and to eliminate noise for a signal measurement. The deactivation period ranges from 128 to 640 microseconds, more preferably from 200 microseconds to 400 microseconds, and more preferably from 225 microseconds to 300 microseconds. In reference to FIG. 6, this deactivation period occurs during block 1300. At block 254, during the deactivation period, the optical sensor 30 is activated to obtain multiple readings using the light source 135 and the photodetector 130. Preferably 4 to 25 sub-readings or sub-samples are obtained during the deactivation period. The sub-readings or sub-samples are averaged for noise reduction to provide a reading or sample value. In a single second, from 500 to 1500 sub-readings or sub-samples are obtained by the optical sensor 30. At block 256, the processor 41 is reactivated and the reading values are processed by processor 41. At block 258, heart rate data is generated from the readings by the processor 41. At block 260, health related data is generated from the heart rate data, and the health related data and the heart rate data are displayed on the display member 40.

Figure 14:
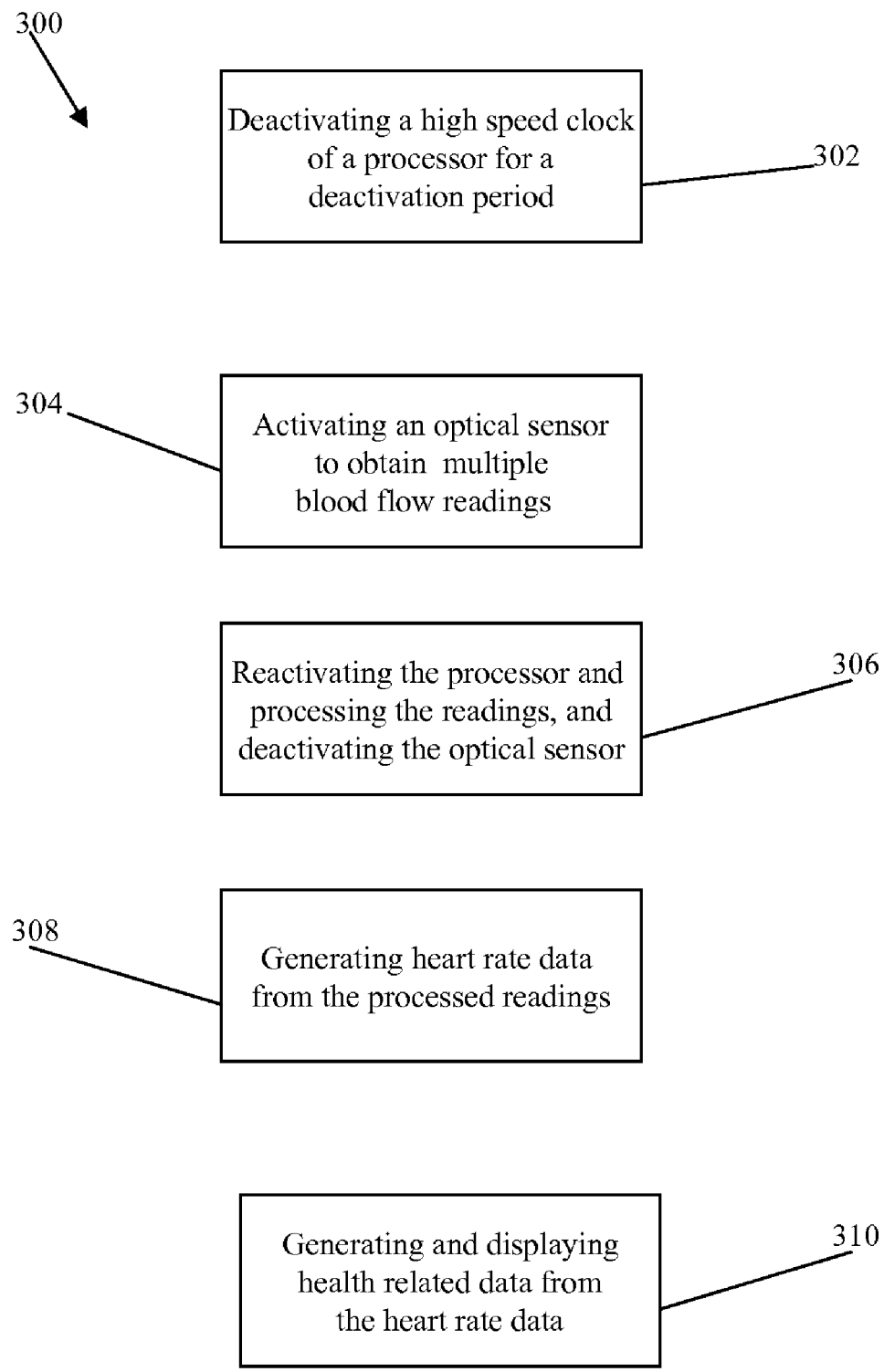
FIG. 14 is a flow chart of a specific noise reduction method of the present invention.
Figure 15:
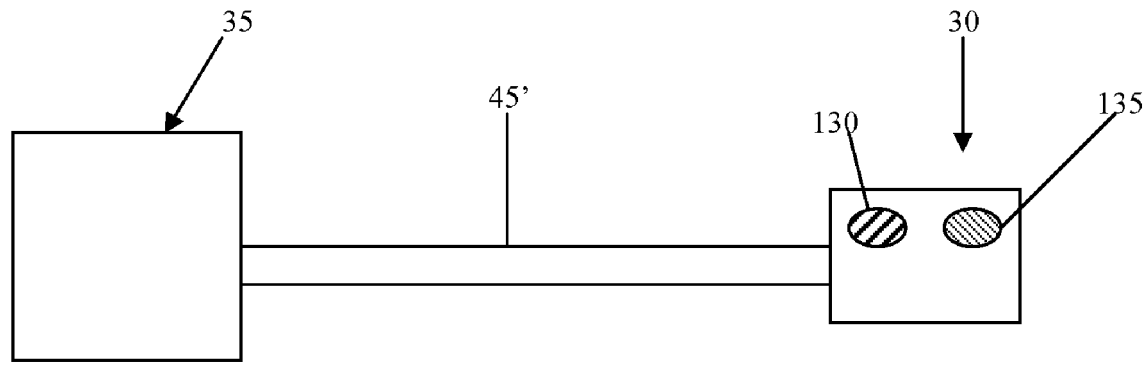
FIG. 15 is a schematic diagram of a prior art connection of a processor to an optical sensor.

FIG. 14 illustrates a more specific method 300 for noise reduction during a signal reading. At block 302, a high speed clock of a processor 41 is deactivated for a deactivation period as discussed above. At block 304, the optical sensor 30 is activated during the deactivation period to obtain multiple readings as discussed above. At block 306, the processor 41 is reactivated and the readings are processed. The optical sensor 30 is also deactivated. At block 308, heart rate data is generated from the readings by the processor 41. At block 310, health related data is generated from the heart rate data, and the health related data and the heart rate data are displayed on the display member 40.

Figure 17:
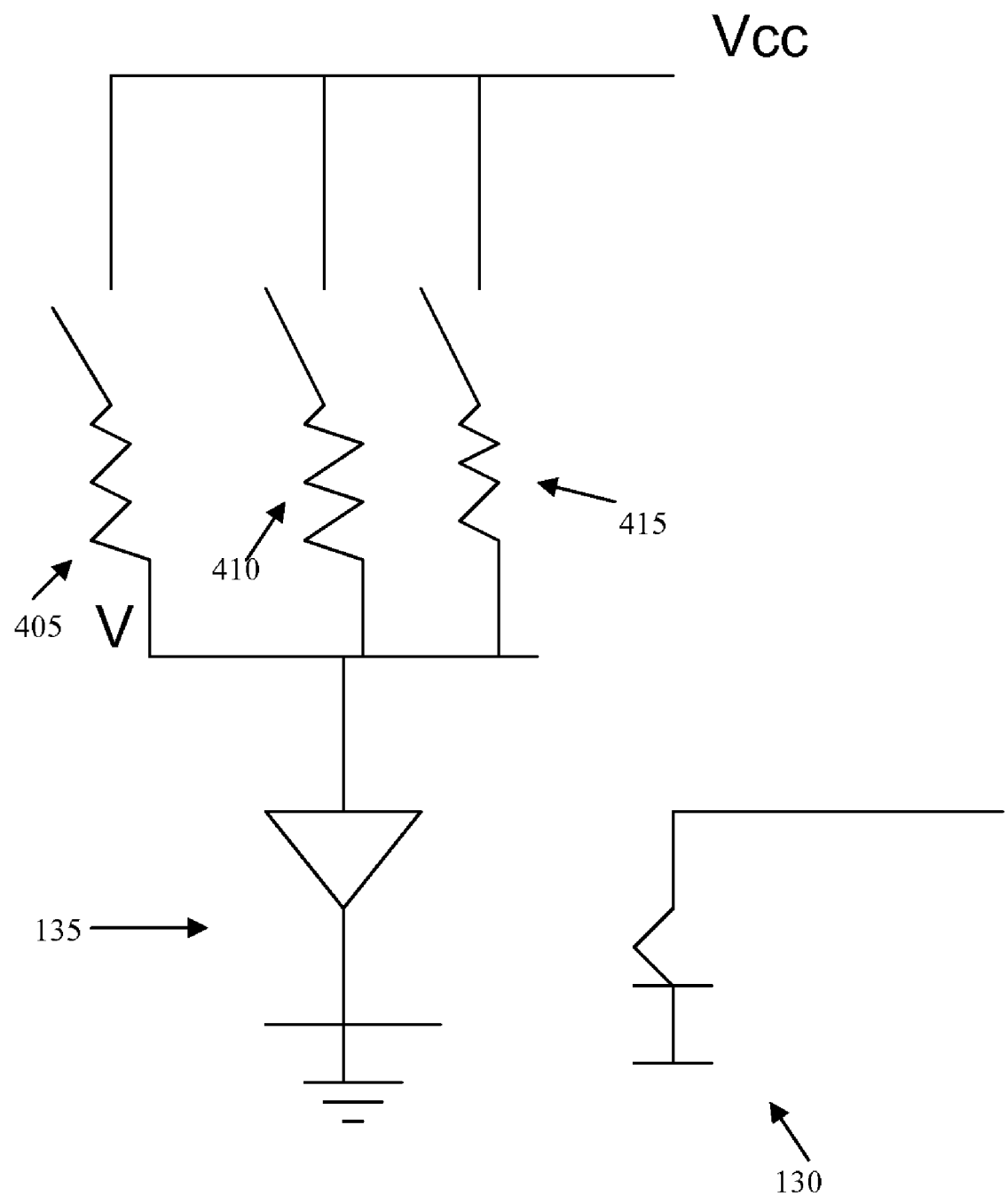
FIG. 17 is a schematic diagram of a light source intensity controlling mechanism of the present invention.

FIG. 17 illustrates a mechanism for controlling the intensity of the light source 135 using a plurality of resistors 405, 410 and 415 in parallel. Usually, an optical sensor 30 has a light source 135 set for a single intensity for placement at a single location on a typically user. However, if the optical sensor 30 is positioned differently or if the user is not a typical user, then the intensity of the light source 135 may be too great for the photodetector 130 and lead to saturation of the photodetector 130 which terminates the signal reading. The present invention preferably adjusts the intensity of the light source 135 using feedback from the photodetector 130 to indicate whether the light intensity is too high or too low. As shown in FIGS. 17,17A, 17B and 17C, the current flow through the resistors 405, 410 and 415 is changed, which results in changes in the light intensity of the light source 135. Equation A below illustrates the resistance:

$$1/R_{\mathit{eff}} = S_1(1/R_1) + S_2(1/R_2) + S_3(1/R_3)$$

where $S_n$=Switch$_n$ having a value of 0 or 1, and $R_n$=resistor, in ohms. In one embodiment, resistor 405 has a resistance of 400 Ohms, resistor 410 has a resistance of 200 Ohms and resistor 415 has a resistance of 100 Ohms. Various combinations of the resistors can be switched on to control the light intensity.

Figure 17A:
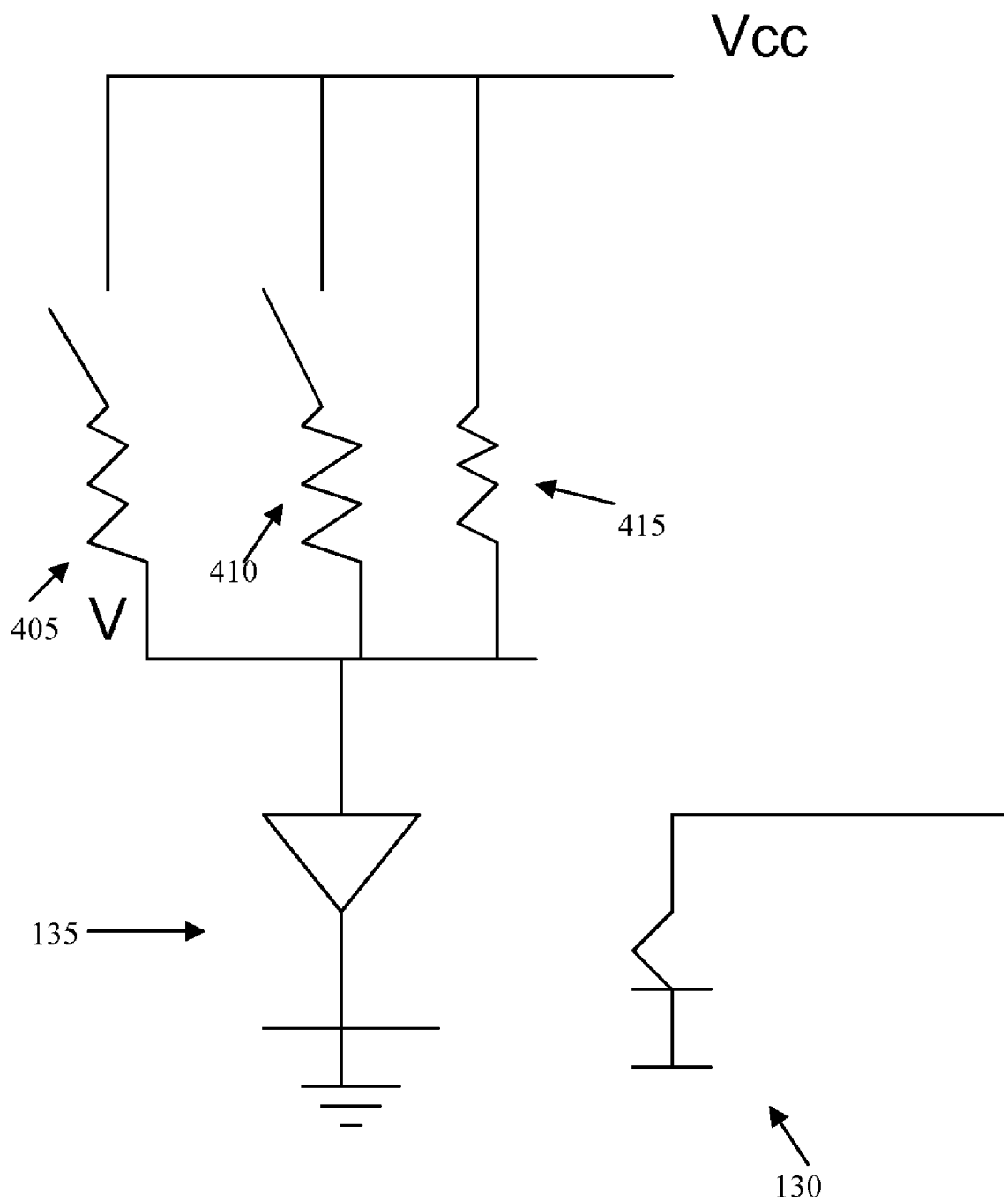
FIG. 17A is a schematic diagram of the light source intensity controlling mechanism of FIG. 17 with a single resistor connected.
Figure 17B:
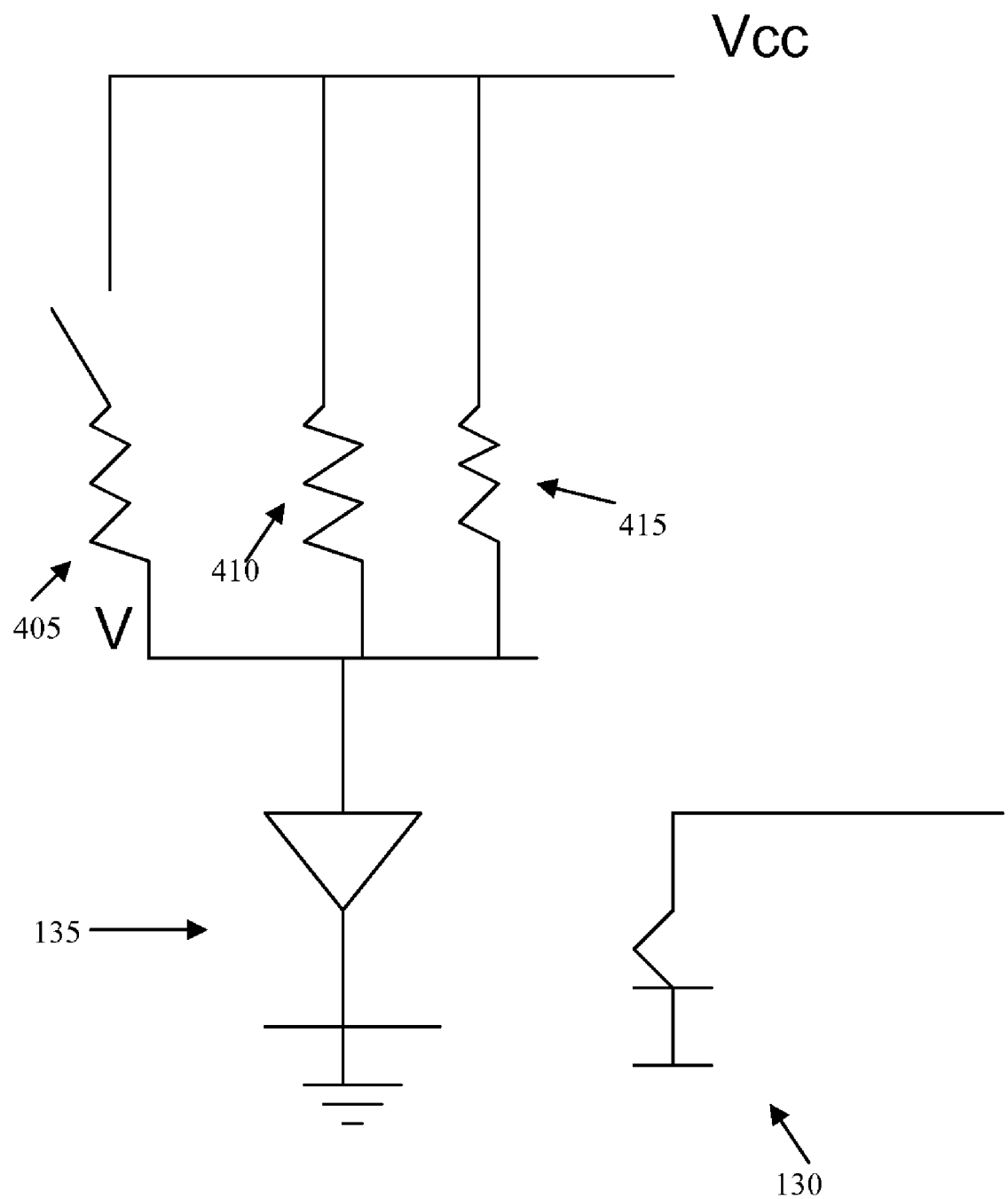
FIG. 17B is a schematic diagram of the light source intensity controlling mechanism of FIG. 17 with two resistors connected.
Figure 17C:
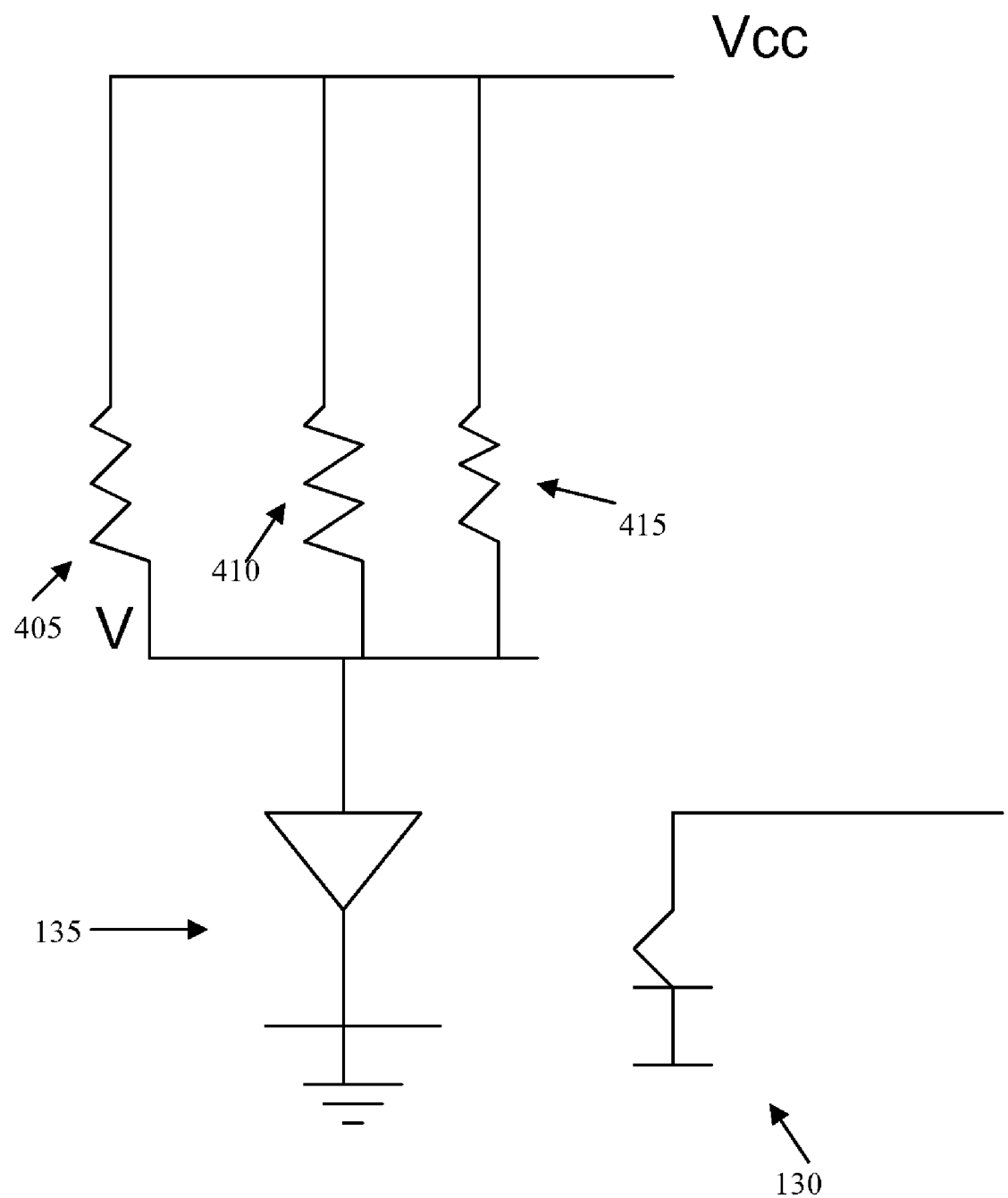
FIG. 17C is a schematic diagram of the light source intensity controlling mechanism of FIG. 17 with all resistors connected.

FIG. 17A has current flowing through a single line and a single resistor. FIG. 17C has current flowing through all of the lines. Although FIG. 17C utilizes the most resistors 405, 410 and 415, it has the greatest current flow and the highest intensity. The current flow is given by the equation B:

$$(V_{cc}-V)/R_{eff}=I_{LED}$$

where $I_{LED}$ is the current flow. Although only three resistors are shown, those skilled in the pertinent art will recognize that more or fewer resistors may be used without departing from the scope and spirit of the present invention.

Figure 18:
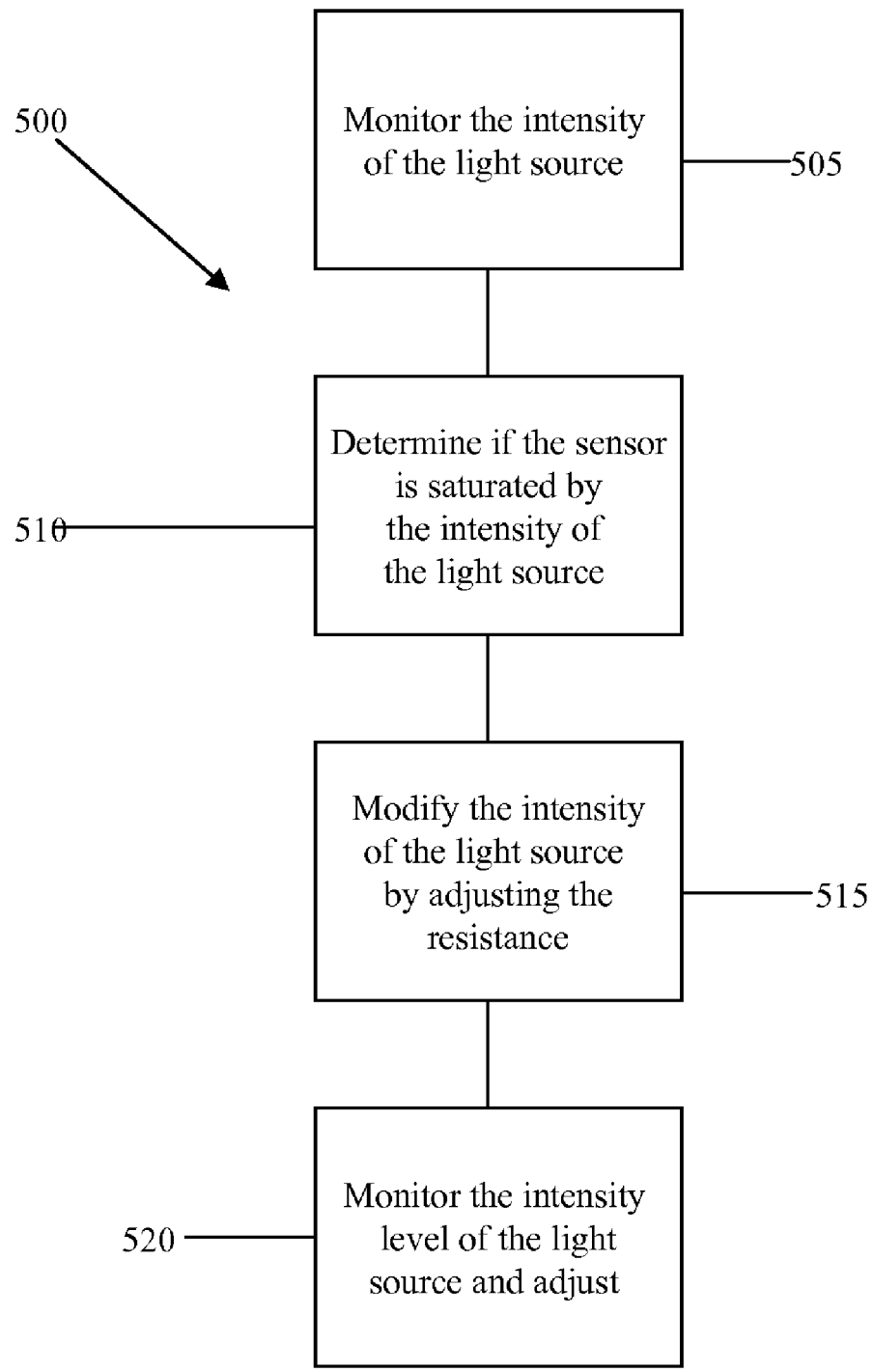
FIG. 18 is a flow chart of a light source intensity controlling method of the present invention.

FIG. 18 is a preferred method 500 for controlling the light intensity of the optical sensor 30. At block 505, the light intensity of the light source 135 is monitored. At block 510, the sensor/photodetector is determined to be saturated by the light source. At block 515, the intensity of the light source is modified by adjusting the resistance and the flow of current to the light source 135. At block 520, the light intensity is again monitored and adjusted if necessary. In a preferred embodiment, this automatic gain mechanism prevents the green light from overwhelming the photodetector thereby maintaining an accurate reading no matter where the optical sensor is placed on the user.

Figure 19:
FIG. 19 is a graph illustrating the method and mechanism of controlling the intensity of the light source over time.

FIG. 19 illustrates how the control mechanism operates to maintain a proper light intensity. As the signal reaches the upper limit, the photodetector becomes saturated and the processor lowers the current flow, which results in a break in the signal. Then as the signal is lowered it becomes too low and the processor increases the light intensity resulting in a break in the signal.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method of a providing a real-time heart rate for a user, the method comprising:
    generating a signal corresponding to the flow of blood through an anterior ethmoidal artery of the user, the signal generated from an optical sensor in proximity to the anterior ethmoidal artery of the user, the optical sensor integrated on eyewear worn by the user, the eyewear comprising a lens support portion, a pair of lenses positioned within the lens support portion, a first temporal member attached and extending from the lens support portion, a second temporal member attached and extending from the lens support portion a first nose support attached to the lens support portion and a second nose support attached to the lens supporting portion, wherein the optical sensor comprises a light source integrated into the first nose support and a photodiode integrated into the second nose support;
    transmitting the signal from the optical sensor through a connection cable to a digital storage and processing device;
    processing the signal at the digital storage and processing device using an adaptive algorithm to obtain a real-time heart rate for the user, the processing comprising deactivating a processor for a deactivation period, activating the optical sensor during the deactivation period to generate a signal corresponding to the flow of blood through the anterior ethmoidal artery of the user, reactivating the processor after the deactivation period to generate real-time heart rate data of the user from the signal generated by the optical sensor, processing the real-time heart rate data of the user for analysis of a plurality of real-time vital signs of the user including calories expended by the user, and for real-time display of a plurality of the user's vital signs; and
    displaying the real-time heart rate and a plurality of the user's vital signs on a display member disposed on an exterior surface of the digital storage and processing device, the display of the real-time heart rate and the plurality of user's vital signs controlled by the user using a control component extending from the digital storage and processing device.

2. The method according to claim 1 wherein the digital storage and processing device is a MP3 player.

3. The method according to claim 1 wherein the optical sensor comprises a green LED light source which generates a wavelength at approximately 567 nanometers and a light-to-voltage converter.

4. A monitoring device for monitoring the health of a user, the monitoring device comprising:
    eyewear comprising a lens support portion, a pair of lenses positioned within the lens support portion, a first temporal member attached and extending from the lens support portion, a second temporal member attached and extending from the lens support portion a first nose support attached to the lens support portion and a second nose support attached to the lens supporting portion;
    an optical sensor comprising a light source integrated into the first nose support and a photodiode integrated into the second nose support;
    a digital storage and processing device comprising a microprocessor, a control component and a display member, the digital storage and processing configured to use an adaptive algorithm to process a signal generated by the optical sensor corresponding to the flow of blood through an anterior ethmoidal artery of a user by deactivating the microprocessor for a deactivation period, activating the optical sensor during the deactivation period to generate a signal corresponding to the flow of blood through the anterior ethmoidal artery of the user, reactivating the microprocessor after the deactivation period to generate real-time heart rate data of the user from the signal generated by the optical sensor, processing the real-time heart rate data of the user for analysis of a plurality of real-time vital signs of the user comprises calories expended by the user for real-time display on the display member;
    a connection cable transmitting a signal from the optical sensor to the digital storage and processing device.

5. The monitoring device according to claim 4 wherein the optical sensor comprises a light-to-voltage photodetector capable of transmitting a signal, and at least one light emitting diode capable of radiating light ranging from 550 nanometers to 1100 nanometers.

6. The monitoring device according to claim 4 wherein the plurality of the user's vital signs further comprises the user's heart rate, a target zone and accumulated calories expended over a set time period.

7. The monitoring device according to claim 4 wherein the digital storage and processing device is a MP3 player.

* * * * *